United States Patent
Braddock et al.

(10) Patent No.: US 9,867,870 B2
(45) Date of Patent: *Jan. 16, 2018

(54) COMPOSITIONS AND METHODS FOR TREATING HEMOPHILIA

(71) Applicant: YALE UNIVERSITY, New Haven, CT (US)

(72) Inventors: Demetrios Braddock, Guilford, CT (US); Ronald Albright, Hamden, CT (US)

(73) Assignee: Yale University, New Haven, CT (US)

(*) Notice: Subject to any disclaimer, the term of this patent is extended or adjusted under 35 U.S.C. 154(b) by 0 days.

This patent is subject to a terminal disclaimer.

(21) Appl. No.: 15/480,986

(22) Filed: Apr. 6, 2017

(65) Prior Publication Data

US 2017/0274054 A1   Sep. 28, 2017

Related U.S. Application Data

(63) Continuation of application No. 14/358,166, filed as application No. PCT/US2012/064997 on Nov. 14, 2012, now Pat. No. 9,642,896.

(60) Provisional application No. 61/703,687, filed on Sep. 20, 2012, provisional application No. 61/559,461, filed on Nov. 14, 2011.

(51) Int. Cl.
*A61K 38/46* (2006.01)
*A61K 45/06* (2006.01)
*C12N 9/14* (2006.01)
*C12N 9/22* (2006.01)

(52) U.S. Cl.
CPC .............. *A61K 38/46* (2013.01); *A61K 45/06* (2013.01); *C12N 9/14* (2013.01); *C12N 9/22* (2013.01); *C12Y 301/04001* (2013.01); *C12Y 306/01009* (2013.01)

(58) Field of Classification Search
None
See application file for complete search history.

(56) References Cited

U.S. PATENT DOCUMENTS

| 9,642,896 | B1* | 5/2017 | Braddock | A61K 38/46 |
| 2010/0184672 | A1 | 7/2010 | McCarty et al. | |
| 2010/0240583 | A1* | 9/2010 | Tada | A61K 31/7088 514/2.8 |

OTHER PUBLICATIONS

Printout of bleeding disorers from the American Society of Hematology, downloaded Sep. 11, 2017 from world wide web.hematology.org/Patients?Bleeding.aspx, 5 pages.*
Albright, et al., "NPP4 is a procoagulant enzyme on the surface of vascular endothelium", Blood. 120(22), 2012, 4432-4440.
Gijsbers, et al., "The hydrolysis of lysophospholipids and nucleotides by autotaxin (NPP2) involves a single catalytic site", FEBS Lett. 538(1-3), 2003, 60-64.
Goding, et al., "Physiological and pathophysiological functions of the ecto-nucleotide pyrophosphatase/phosphodiesterase family", Biochim Biophys Acta. 1638(1), 2003, 1-19.
Goldman, et al., "Hydrolysis of diadenosine 5',5"-P',P"-triphosphate (Ap3A) by porcine aortic endothelial cells", Circ Res. 59(3), 1986, 362-366.
Jansen, et al., "Proteolytic maturation and activation of autotaxin (NPP2), a secreted metastasis-enhancing lysophospholipase D", J Cell Sci. 118(Pt 14), 2005, 3081-3089.
Luthje, et al., "Diadenosine triphosphate (Ap3A) mediates human platelet aggregation by liberation of ADP", Biochem Biophys Res Commun. 118(3), 1984, 704-709.
Niagase, et al., Uniprot Submission Accession No. Q9Y6X5 (online at <www.uniprot.org/uniprot/Q9Y6X5.txt?version=66>), 2011.
Ogilvie, et al., "Identification and partial characterization of an adenosine(5')tetraphospho(5')adenosine hydrolase on intact bovine aortic endothelial cells", Biochem J. 259(1), 1989, 97-103.
Sakagami, et al., "Biochemical and molecular characterization of a novel choline-specific glycerophosphodiester phosphodiesterase belonging to the nucleotide pyrophosphatase/phosphodiesterase family", J Biol Chem. 280(24), 2005, 23084-23093.
Saunders, et al., "Kinetic analysis of autotaxin reveals substrate-specific catalytic pathways and a mechanism for lysophosphatidic acid distribution", J Biol Chem. 286(34), 2011, 30130-30141.
Vollmayer, et al., "Hydrolysis of diadenosine polyphosphates by nucleotide pyrophosphatases/phosphodiesterases", Eur J Biochem. 270(14), 2003, 2971-2978.

* cited by examiner

*Primary Examiner* — Michael Szperka
(74) *Attorney, Agent, or Firm* — Saul Ewing Arnstein & Lehr LLP; Kathryn Doyle; Domingos J. Silva

(57) ABSTRACT

The present invention relates to compositions and methods for modulating coagulation through modulating the level or activity of NPP4.

7 Claims, 9 Drawing Sheets

COMPOSITIONS AND METHODS FOR TREATING HEMOPHILIA

CROSS-REFERENCE TO RELATED APPLICATIONS

The present application is a continuation of, and claims priority to, U.S. patent application Ser. No. 14/358,166, filed May 14, 2014, now issued as U.S. Pat. No. 9,642,896, which is a 35 U.S.C. §371 national phase application from, and claiming priority to, International Application No. PCT/US2012/064997, filed Nov. 14, 2012, and published under PCT Article 21(2) in English, which claims priority to U.S. Provisional Patent Application No. 61/559,461, filed Nov. 14, 2011, and to U.S. Provisional Patent Application No. 61/703,687, filed Sep. 20, 2012, all of which applications are incorporated by reference herein in their entireties.

BACKGROUND OF THE INVENTION

The formation of a platelet-rich thrombus stabilized by fibrin crosslinking is the final common pathway for arterial thrombosis, the most common disease process affecting adults in the United States. The first step in thrombus formation consists of platelet adhesion to the exposed sub-endothelial extracellular matrix at the site of vascular injury. Here, circulating blood platelets bind collagen via their GPVI receptors, and bind von Willebrand factor via GPIb, triggering inside-out activation of other surface integrins and the release of platelet granule contents into the extracellular space (Nieswandt and Watson, 2003, Blood 102:449-61). The release of preformed molecules stored in platelet dense granules such as ADP, serotonin, and ionized calcium, then amplifies the clotting reaction beyond the platelet monolayer bound on the collagen surface to circulating platelets in the immediate vicinity of the damaged endothelium. This amplification is further augmented by the secretion of thromboxane A2. ADP binding to purinergic receptors on the platelet surface (P2Y1, and P2Y12), induces rapid calcium influx and mobilization resulting in platelet shape change, activation and partial degranulation thus promoting platelet aggregation. Upon granule release, local ADP concentrations are estimated to exceed 500 $\mu$M, but ADP is quickly metabolized by ectoenzymes on the surface of endothelial cells (such as CD39 (Marcus et al., 1997, Journal of Clinical Investigation, 99:1351-60; Knowles, 2011, Purinergic Signalling 7:21-45) and soluble phosphohydrolases in blood plasma which attenuate the prothrombotic response (Pearson and Gordon, 1985, Annu Rev Physiol 47:617-27; Birk et al., 2001, J Lab Clin Med, 139:116-124; Kaczmarek et al., 1996, J Biol Chem 271:33116-22; Yegutkin, 2008, Biochim Biophys Acta 1783:673-94). To sustain the clotting reaction, a slow and steady source of ADP at the site of the growing thrombus is required. Another preformed chemical released by platelet dense granules at high concentrations, diadenosine triphosphate (Ap3A), has an ill-defined role in thrombus formation but has been suggested to provide a source of long lasting ADP at the site of vascular injury.

Ap3A is stored within platelet granules at high concentrations (e.g., about 20-30 mM) and is released with ADP and ATP into the blood during thrombin-induced platelet aggregation at concentrations thought to range between 40-100 $\mu$M (Luthje et al., 1987, Blut 54:193-200). Turbidometric studies in citrated platelet-rich plasma (PRP) demonstrate that 10-20 $\mu$M Ap3A induces weak platelet aggregation in a slow but persistent manner (Luthje and Ogilvie, 1984, Biochem Biophys Res Commun 118:704-9). The mechanism by which Ap3A promotes aggregation suggests that Ap3A is stored as a metabolically inactive or 'chemically masked' molecule, which upon release into the extracellular space is converted into a hemodynamically active form by an enzyme that liberates ADP from the dinucleotide. An enzyme capable of hydrolyzing Ap3A into AMP and ADP was partially characterized on the surface of intact porcine (Goldman et al., 1986, Circ Res 59:362-6) and bovine (Ogilvie et al., 1989, Biochem J 259:97-103) vascular endothelial cells over 20 years ago. Prior to this, Luthje and Olgilvie linked weak Ap3A hydrolase activity in PRP to an extracellular glycoprotein, neither stored within nor released by platelets, with optimal enzymatic activity around pH 8.5 to 9.0, and a divalent cation-dependence (Luthje and Ogilvie, 1987, Eur J Biochem 169:385-8). The inability to further characterize and purify the enzyme impeded direct experimentation of the enzyme's effect on platelet activation and aggregation.

The human ectonucleotide pyrophosphatase/phosphodiesterase (ENPP or NPP) family consists of seven extracellular, glycosylated proteins (NPP1-7) that hydrolyze phosphodiester bonds. NPPs are cell surface enzymes, with the exception of NPP2, which is exported to the plasma membrane but cleaved by furin and released into the extracellular fluid (Jansen et al., 2005, J Cell Sci 118:3081-9). A subset of the family (NPP1-3) can recognize 5' nucleotide-containing substrates and, approximately 10 years ago, were also reported to hydrolyze diadenosine polyphosphates, including Ap3A and Ap4A, into AMP and related products (Vollmayer et al., 2003, Eur J Biochem 270:2971-8). In that study, the activity of NPP1 and NPP3 was measured by purifying membrane fractions of Chinese hamster ovary (CHO) cells stably transfected with the enzymes, while the soluble form of NPP2 was prepared from vaccinia virus lysate of BS-C-1 cells. The investigators reported that all NPPs tested hydrolyzed Ap3A with comparable rates and Michaelis constants (Km) in the low uM range (Vollmayer et al., 2003, Eur J Biochem 270:2971-8).

The effects of NPP enzymes on hemostasis and coagulation have never been directly demonstrated. In addition, the uncertainty regarding the precise role of NPPs in thrombosis has led to their inclusion alongside ADP-metabolizing enzymes (such as CD39) in some studies (Spanevello et al., 2010, Clin Chim Acta 411:210-4; Spanevello et al., 2010, J Neurol 257:24-30), giving the impression that their enzymatic activities are associated with antithrombotic effects resulting from ADP metabolism.

Despite the advances made in the art of bleeding and coagulation, there is a need in the art for novel compositions and methods for modulating bleeding and coagulation. The present invention fulfills these needs.

SUMMARY OF THE INVENTION

The present invention relates to compositions and methods for modulating coagulation through modulating the level or activity of NPP4.

In one embodiment, the invention is a method of treating bleeding in a subject including administering to the subject a therapeutically effective amount of a composition comprising at least one agent, wherein the at least one agent is at least one selected from the group consisting of an NPP4 polypeptide, an NPP4 polypeptide fragment, an NPP4 polypeptide derivative, and an activator of NPP4. In some embodiments, the NPP4 polypeptide is a soluble, recombinant NPP4 polypeptide. In other embodiments, the NPP4 fragment is an NPP4 polypeptide that lacks the NPP4 transmembrane domain. In a particular embodiment, the NPP4 fragment comprises amino acid residues 1-407 of SEQ ID NO:1. In another particular embodiment, the NPP4 fragment consists of amino acid residues 1-407 of SEQ ID NO:1. In some embodiments, the at least one agent is administered in combination with at least one other agent useful in treating bleeding. In various embodiments, the at least one agent is administered acutely or chronically. In various embodiments, the at least one agent is administered locally, regionally or systemically. In some embodiments, the activator of NPP4 is an activator of NPP4 expression. In other embodiments, the activator of NPP4 is an activator of NPP4 activity. In various embodiments, the activator of NPP4 is at least one of a chemical compound, a protein, a peptide, a peptidomemetic, or a small molecule chemical compound. In a particular embodiment, the subject is human.

In another embodiment, the invention is a method of treating a coagulopathy in a subject including administering to the subject a therapeutically effective amount of a composition comprising at least one agent, wherein the at least one agent is at least one selected from the group consisting of an NPP4 polypeptide, an NPP4 polypeptide fragment, an NPP4 polypeptide derivative, and an activator of NPP4. In some embodiments, the NPP4 polypeptide is a soluble, recombinant NPP4 polypeptide. In other embodiments, the NPP4 fragment is an NPP4 polypeptide that lacks the NPP4 transmembrane domain. In a particular embodiment, the NPP4 fragment comprises amino acid residues 1-407 of SEQ ID NO:1. In another particular embodiment, the NPP4 fragment consists of amino acid residues 1-407 of SEQ ID NO:1. In some embodiments, the at least one agent is administered in combination with at least one other agent useful in treating bleeding. In various embodiments, the at least one agent is administered acutely or chronically. In various embodiments, the at least one agent is administered locally, regionally or systemically. In some embodiments, the activator of NPP4 is an activator of NPP4 expression. In other embodiments, the activator of NPP4 is an activator of NPP4 activity. In various embodiments, the activator of NPP4 is at least one of a chemical compound, a protein, a peptide, a peptidomemetic, or a small molecule chemical compound. In a particular embodiment, the subject is human. In various embodiments, the coagulopathy is associated with at least one selected from the group consisting of a genetic disorder, NSAID-associated coagulopathy, thrombocytopenia, Glanzmann's thrombasthenia, Bernard-Soulier syndrome, Von Willebrand's Disease, Hemophilia, Platelet Storage Pool Deficiency, Gray Platelet Syndrome, Quebec Platelet Disorder, Delta Storage Pool Deficiency, Hermasky-Publak Syndrome, and Chediak-Higashi Syndrome.

In one embodiment, the invention is a method of treating thrombosis in a subject including administering to the subject a therapeutically effective amount of an inhibitor of NPP4. In some embodiments, the inhibitor of NPP4 is an inhibitor of NPP4 expression. In other embodiments, the inhibitor of NPP4 is an inhibitor of NPP4 activity. In various embodiments, the inhibitor of NPP4 is at least one of a chemical compound, a protein, a peptide, an antibody, a peptidomemetic, an antisense nucleic acid, a ribozyme, or a small molecule chemical compound. In a particular embodiment, the inhibitor of NPP4 is an antibody that specifically binds to NPP4. In various embodiments, the antibody is at least one of a polyclonal antibody, a monoclonal antibody, an intracellular antibody, an antibody fragment, a single chain antibody (scFv), a heavy chain antibody, a synthetic antibody, a chimeric antibody, or a humanized antibody. In various embodiments, the thrombosis is associated with at least one selected from the group consisting of a genetic disorder, venous thrombosis, deep vein thrombosis, portal vein thrombosis, renal vein thrombosis, jugular vein thrombosis, Budd-Chiari Syndrome, Paget-Schroetter Disease, cerebral venous sinus thrombosis, arterial thrombosis, coronary artery disease, peripheral vascular disease, stroke, and myocardial infarction. In some embodiments, the inhibitor of NPP4 is administered in combination with another agent useful in inhibiting thrombosis. In some embodiments, the inhibitor of NPP4 is administered acutely or chronically. In various embodiments, the inhibitor of NPP4 is administered locally, regionally or systemically. In a particular embodiment, the subject is human.

In another embodiment, the invention is a method of inhibiting thrombosis in a subject including administering to the subject a therapeutically effective amount of an inhibitor of NPP4. In some embodiments, the inhibitor of NPP4 is an inhibitor of NPP4 expression. In other embodiments, the inhibitor of NPP4 is an inhibitor of NPP4 activity. In various embodiments, the inhibitor of NPP4 is at least one of a chemical compound, a protein, a peptide, an antibody, a peptidomemetic, an antisense nucleic acid, a ribozyme, or a small molecule chemical compound. In a particular embodiment, the inhibitor of NPP4 is an antibody that specifically binds to NPP4. In various embodiments, the antibody is at least one of a polyclonal antibody, a monoclonal antibody, an intracellular antibody, an antibody fragment, a single chain antibody (scFv), a heavy chain antibody, a synthetic antibody, a chimeric antibody, or a humanized antibody. In various embodiments, the thrombosis is associated with at least one selected from the group consisting of a genetic disorder, venous thrombosis, deep vein thrombosis, portal vein thrombosis, renal vein thrombosis, jugular vein thrombosis, Budd-Chiari Syndrome, Paget-Schroetter Disease, cerebral venous sinus thrombosis, arterial thrombosis, coronary artery disease, peripheral vascular disease, stroke, and myocardial infarction. In some embodiments, the inhibitor of NPP4 is administered in combination with another agent useful in inhibiting thrombosis. In some embodiments, the inhibitor of NPP4 is administered acutely or chronically. In various embodiments, the inhibitor of NPP4 is administered locally, regionally or systemically. In a particular embodiment, the subject is human.

In one embodiment, the invention is a composition having an agent, wherein the agent is at least one of an isolated NPP4 polypeptide, an isolated NPP4 polypeptide fragment, or an isolated NPP4 derivative. In some embodiments, the NPP4 polypeptide is a soluble, recombinant NPP4 polypeptide. In other embodiments, the NPP4 fragment is an NPP4 polypeptide that lacks the NPP4 transmembrane domain. In a particular embodiment, the NPP4 fragment comprises amino acid residues 1-407 of SEQ ID NO:1. In another particular embodiment, the NPP4 fragment consists of amino acid residues 1-407 of SEQ ID NO:1.

In another embodiment, the invention is a method of identifying a test compound as a modulator of NPP4, including the steps of determining the level of NPP4 in the presence of a test compound, determining the level of NPP4 in the absence of a test compound, comparing the level of NPP4 in the presence of the test compound with the level of NPP4 in the absence of the test compound, identifying the test compound as a modulator of NPP4 when the level of NPP4 in the presence of the test compound is different than the level of NPP4 in the absence of the test compound. In some embodiments, when the level of NPP4 is higher in the presence of the test compound, the test compound is identified as an NPP4 activator. In other embodiments, when the level of NPP4 is lower in the presence of the test compound, the test compound is identified as an NPP4 inhibitor. In one embodiment, the level of NPP4 is determined by measuring the level of NPP4 mRNA. In another embodiment, the level of NPP4 is determined by measuring the level of NPP4 polypeptide. In another embodiment, the level of NPP4 is determined by measuring an enzymatic activity of NPP4 polypeptide. In various embodiments, the test compound is at least one of a chemical compound, a protein, a peptide, a peptidomemetic, an antibody, a nucleic acid, an antisense nucleic acid, a ribozyme, or a small molecule chemical compound.

BRIEF DESCRIPTION OF THE DRAWINGS

For the purpose of illustrating the invention, there are depicted in the drawings certain embodiments of the invention. However, the invention is not limited to the precise arrangements and instrumentalities of the embodiments depicted in the drawings.

FIGS. 3A and 3B, depicts the results of experiments assessing steady state Ap3A cleavage by NPP4. (A) Time courses of Ap3A cleavage monitored by absorbance at 259 nm after mixing 200 nM NPP4 with (bottom to top) 2, 44, 125, and 250 μM Ap3A. (B) [AP3A] dependent steady-state AP3A cleavage rate by NPP4 (200 nM). The solid line through the data represents the best fit to a rectangular hyperbola.

FIGS. 4A-4D, depicts the results of experiments demonstrating that NPP4 promotes platelet aggregation in the presence of AP3A. Light transmission aggregometry was used to assess aggregation in response to agonists in platelet rich plasma. Data are shown graphically as percent of light transmittance (y-axis) over time (x-axis). (A) Increasing concentrations of Ap3A demonstrate only a primary wave of aggregation followed by rapid platelet disaggregation. (B) Dose-dependent response of Ap3A in the presence of 100 nM NPP4 demonstrates that low micromolar amounts of Ap3A are sufficient to induce robust platelet aggregation. (C and D): Dose-dependence of NPP4 in the presence of 80 uM Ap3A. Both the primary and secondary waves of platelet aggregation are dependent on NPP4 concentration, without evidence for disaggregation over the 10 minute time course of the experiments. In the absence of NPP4, 80 μM AP3A elicits only a primary wave of aggregation followed by rapid disaggregation (C and D). An inactive mutant form of NPP4 in which the catalytic threonine has been mutated to an alanine (T70A; FIG. 4D) fails to induce aggregation at the 100 nM concentration.

FIGS. 5A-5C, depicts the results of experiments demonstrating that ADP receptor blockade inhibits NPP4/Ap3A-promoted platelet aggregation. The platelet ADP receptors, P2Y1 and P2Y12 were blocked using specific receptor antagonists (MRS 2179 and MRS 2395, respectively) in light transmission aggregometry experiments conducted in the presence of 50 nM NPP4 and 80 μM Ap3A. (A) Increasing concentrations of the P2Y1 receptor antagonist, MRS 2179, showed a dose-dependent inhibition of the platelet aggregation response in the presence of NPP4 and Ap3A. (B) Increasing concentrations of the P2Y12 receptor antagonist, MRS 2395, showed a dose-dependent inhibition of the platelet aggregation response in the presence of NPP4 and Ap3A with complete inhibition by 200 μM MRS 2395. All experiments in this panel were conducted in the presence of 10% DMSO to ensure the solubility of MRS 2395. (C) ADP receptor inhibitors do not appreciably (≤4%) inhibit NPP4 enzymatic activity when added at 200-fold molar excess over NPP4 (100 μM inhibitor to 5 nM NPP4). All errors in measurement are less than 1% of the stated value.

FIGS. 6A-6D, depicts the results of experiments demonstrating that Ap4A and NPP2 fail to elicit platelet aggregation. (A) Light transmission aggregometry demonstrates the lack of effect of Ap4A alone or in conjunction with NPP4 on triggering platelet aggregation. 80 μM Ap3A in the absence of NPP4 triggers a primary wave of aggregation, which is followed by rapid disaggregation, while in the presence of 100 nM NPP4 strong primary and secondary aggregation waves are observed. Conversely, 80 μM Ap4A either in the presence or absence of 100 nM NPP4 does not trigger even a primary wave of aggregation. (B) Ap4A has an inhibitory effect on Ap3A induced platelet aggregation in the presence of NPP4. 100 nM NPP4 alone or in the presence of 80 μM Ap4A does not trigger platelet aggregation, while 100 nM NPP4 in the presence of 80 μM Ap3A triggers platelet aggregation. Addition of 80 μM Ap4A to 100 nM NPP4 and 80 μM Ap3A results in an intermediate degree of platelet aggregation compared to 100 nM NPP4 and 80 μM Ap3A alone, suggesting that Ap4A may compete with Ap3A for the active site of NPP4. Ap4A and its product ATP are also known to inhibit the P2Y12 receptor. (C) NPP2 has no effect on platelet aggregation in the presence of Ap3A. 80 μM Ap3A in the absence of NPP2 triggers a primary wave of aggregation, which is followed by rapid disaggregation. Nearly identical responses are observed with the addition of 100 nM and 200 nM NPP2, suggesting that NPP2 lacks the ability to hydrolyze Ap3A to form ADP. Strong platelet aggregation is observed in the presence of 80 μM Ap3A and 50 nM NPP4. (D) Light transmission and lumi aggregometry performed simultaneously demonstrate strong platelet aggregation and dense granule release, respectively, when platelets are exposed to 100 nM NPP4 and 40 μM Ap3A. LTA curves are shown originating from the top. The corresponding lumi aggregometry curves, generated by bioluminescent determination of ATP, which reacts with firefly luciferin and luciferase, are shown on the bottom. Addition of 40 μM Ap3A alone to PRP results in a primary wave of aggregation, followed by rapid disaggregation and a corresponding lumi aggregometry curve that has an initial small spike at mixing followed by steady decay. A similar pattern is observed when 100 nM of inactive T70A mutant of NPP4 is mixed with 40 μM Ap3A.

In contrast, mixing 100 nM NPP4 with 40 μM Ap3A results in the enzymatic production of ADP causing a primary wave of platelet aggregation to occur, leading to granule release after ~1.5 minutes, detected as a strong surge of luminescence corresponding to the ATP liberated from the dense granules. The secondary wave results in a stable aggregate. Mixing 100 nM NPP4 with 40 μM Ap4A looks quite different. Since no ADP is produced, there is no platelet aggregation and no granule release. Instead, the luminescence detects the slow & steady enzymatic production of ATP from the moment of mixing.

Figure 7:
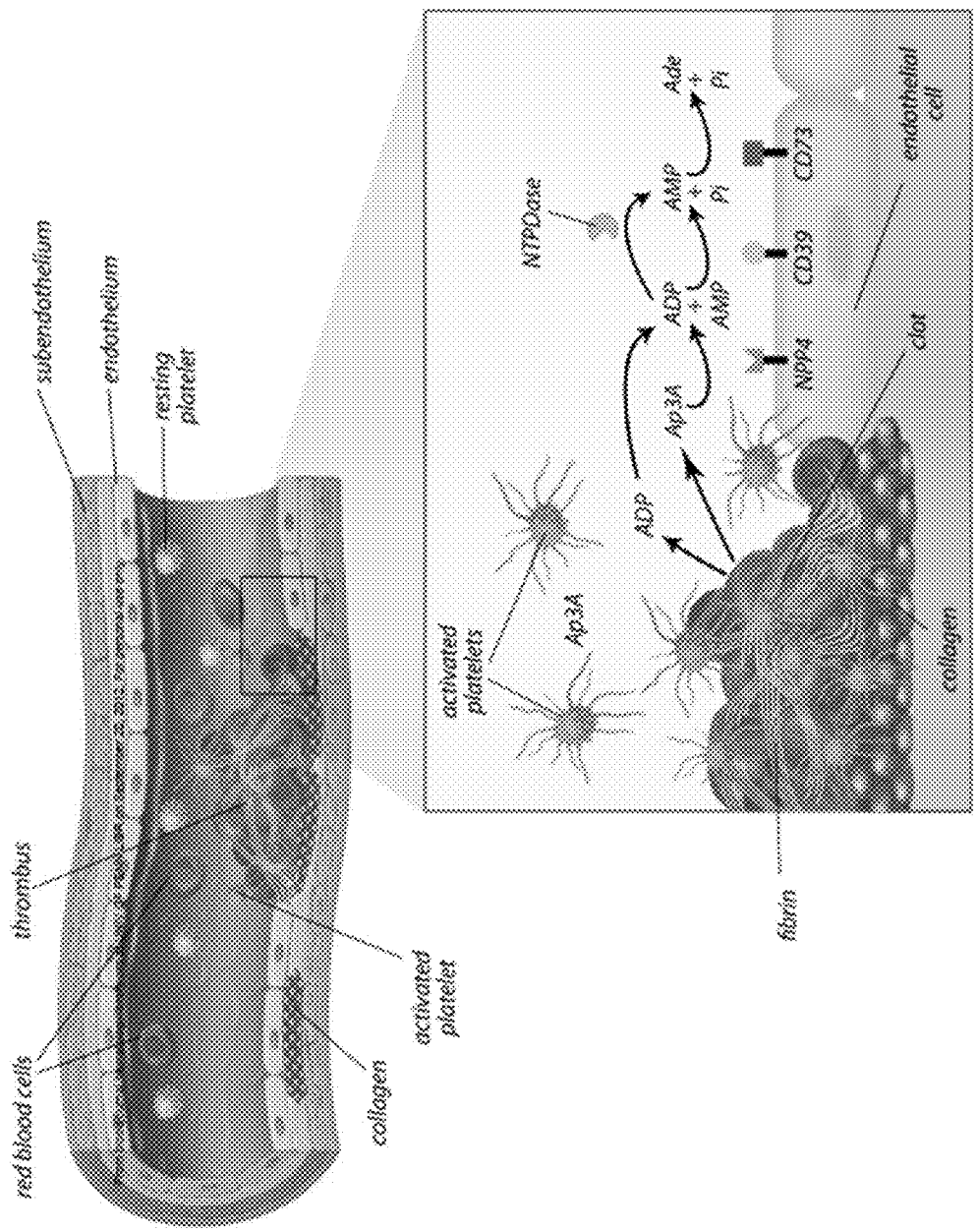

FIG. 7 depicts a schematic of a proposed model of the role of NPP4 in primary hemostasis. In the setting of vascular injury, e.g., due to fracture of a cholesterol plaque, platelets are localized to the site of injury. Binding of platelets to subendothelial collagen leads to platelet shape change, activation and granule release with secretion of calcium ions, ADP and Ap3A into the local area. ADP is metabolized by ectoenzymes (CD39) on the vascular endothelial surface and soluble phosphohydrolyases, reducing the concentrations of ADP in the thrombotic microenvironment. NPP4 bound on the surface of endothelial cells metabolizes Ap3A released by platelets during the second wave of aggregation into ADP, thus increasing the concentration of ADP at the site of the injury. The prolonged release of low-level ADP perpetuates platelet activation and aggregation, resulting in formation of a platelet plug upon which secondary hemostasis reactions occur to form a solid thrombus.

Figure 8:
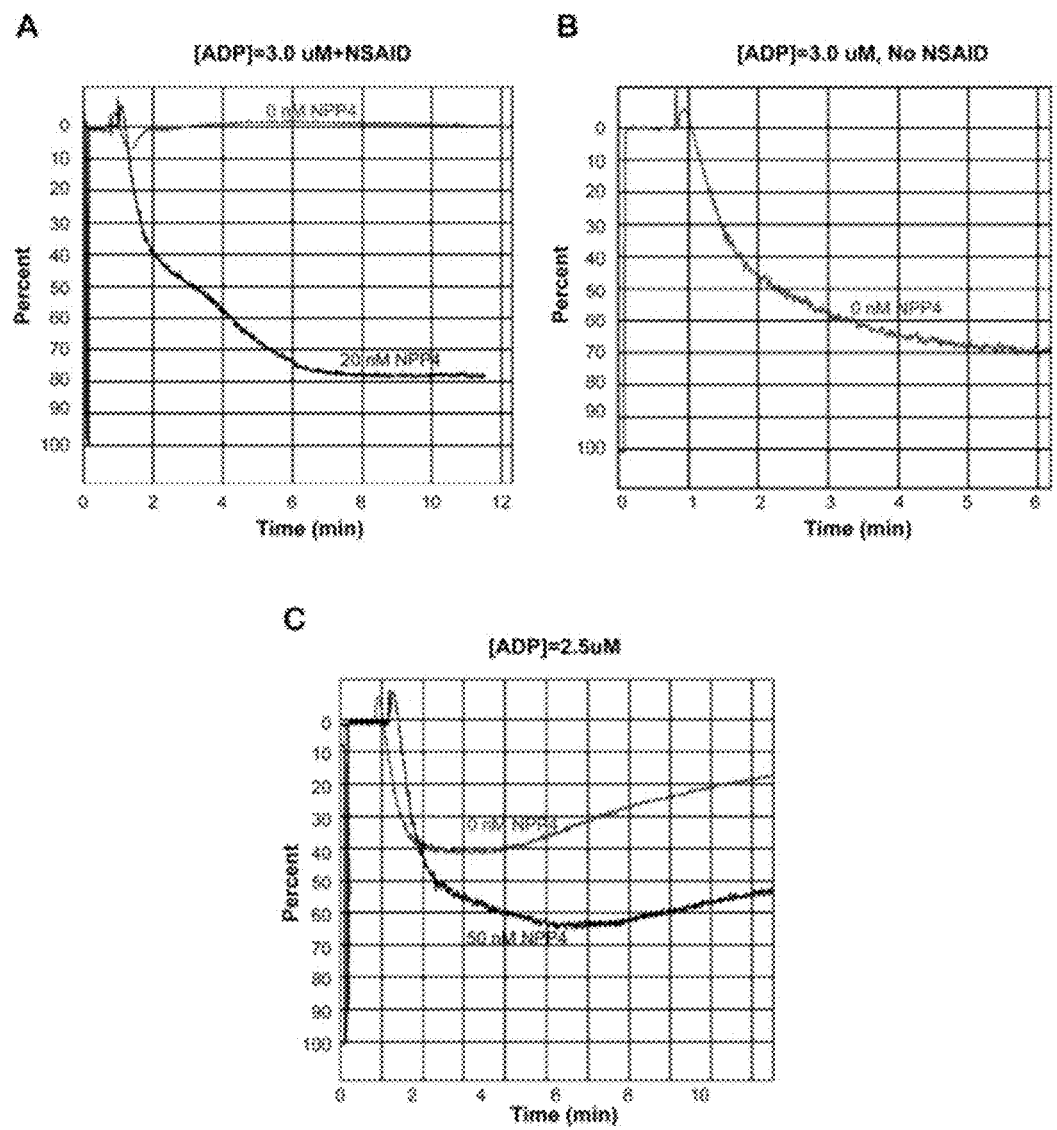

FIG. 8, comprising FIGS. 8A-8C, depicts the results of experiments demonstrating that NPP4 overcomes platelet aggregation deficits induced by NSAIDs and by a storage pool disorder. (A) NPP4 rescues platelets exposed to NSAIDs. Platelet-rich plasma was prepared from blood from an individual who had consumed an 800 mg dose of ibuprofen 12 hours prior to collection. Light transmission aggregometry in the presence of 3 μM ADP shows a primary wave of aggregation followed by rapid disaggregation. Addition of 20 nM NPP4 results in normalization of ADP-induced aggregation, suggesting that low nanomolar levels of NPP4 are able to generate sufficient ADP from Ap3A to rescue platelets that have been affected by NSAID-induced cyclooxygenase-1 inhibition. (B) The aggregation of platelets unexposed to NSAIDs in the presence of 3 uM ADP is shown to compare the aggregation under identical experimental conditions as in FIG. 8A. (C) NPP4 is able to partially overcome a platelet storage pool disorder. Platelet rich plasma was prepared from blood of a patient donor with a mild platelet storage pool disorder. This patient has a mild bleeding diathesis attributed to mild platelet dysfunction in which aggregation in response to arachidonic acid is normal but is nil in response to epinephrine and shows an attenuated secondary wave of aggregation with subsequent disaggregation in response to ADP. Weak aggregation followed by disaggregation is seen in response to 2.5 μM ADP. The addition of 50 nM NPP4 improves maximum amplitude of aggregation from approximately 40% to approximately 65% with less prominent disaggregation noted over the 10-minute time course of the experiment. These results suggest that in storage pool disorders there are sufficient quantities of Ap3A released to react with low nanomolar levels of NPP4 to trigger a physiologic response.

Figure 9:
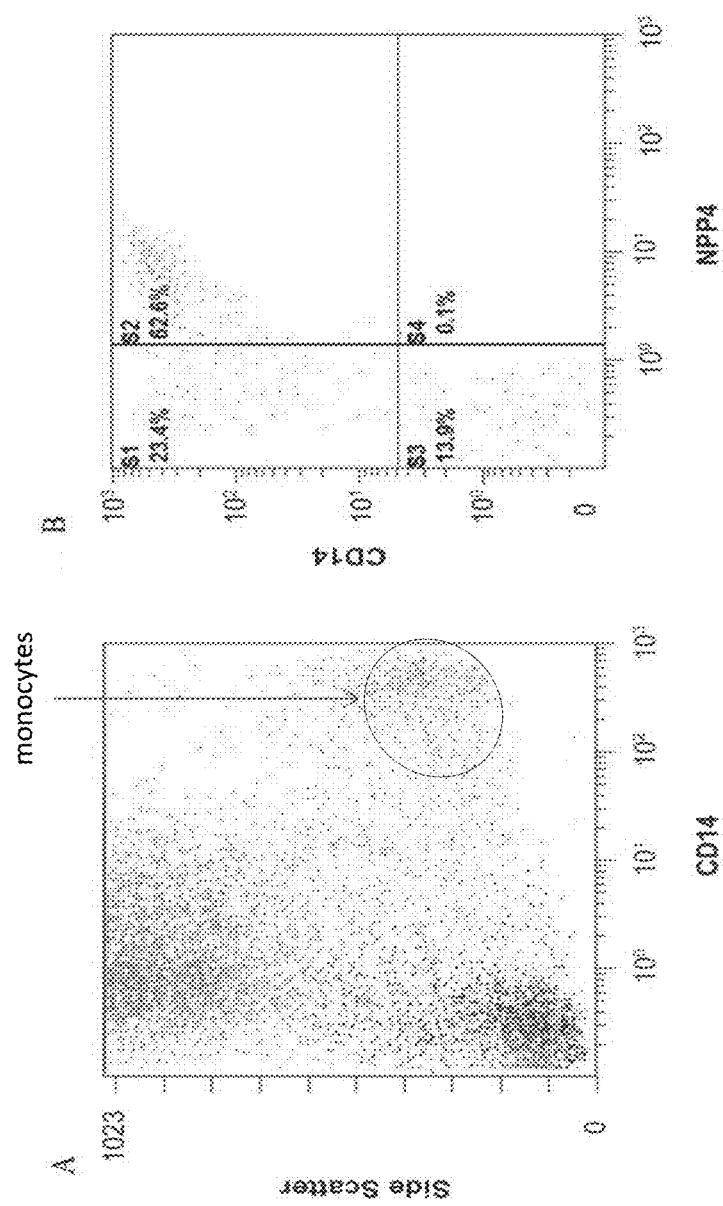

FIG. 9, comprising FIGS. 9A and 9B, depicts the results of an experiment demonstrating that NPP4 is present on the surface of monocytes. (A) Bone marrow flow cytometry showing side scatter vs. CD14 to identify monocytes. (B) Monocyte gate further analyzed with CD14 vs. NPP4 reveals that over 70% of the CD14 positive monocytes also express NPP4. Total events=40,000.

DETAILED DESCRIPTION OF THE INVENTION

The present invention relates to the discovery that NPP4 is located on the walls of blood vessels and activates platelet degranulation and platelet aggregation at low concentrations through the liberation of ADP from Ap3A. Thus, in some embodiments, the invention relates to compositions and methods for increasing the activity of NPP4 to promote platelet degranulation, platelet aggregation, and coagulation, while in other embodiments, the invention relates to compositions and method for decreasing the activity of NPP4 to diminish platelet degranulation, platelet aggregation and coagulation.

In some embodiments, the compositions and methods of the invention relate to activators of NPP4. The compositions and methods of the invention include compositions and methods for treating or preventing disorders and diseases where an increased activity or level of NPP4 is desirable. In various embodiments, the disorders and diseases where an increased activity or level of NPP4 is desirable which can be treated or prevented with the compositions and methods of the invention include diseases and disorders where the promotion of coagulation is desirable, including, but not limited to, bleeding, coagulopathy, including coagulopathy due to a genetic defect, NSAID-associated coagulopathy, thrombocytopenia, Glanzmann's thrombasthenia, Bernard-Soulier syndrome, Von Willebrand's Disease, Hemophilia, Platelet Storage Pool Deficiency, Gray Platelet Syndrome, Quebec Platelet Disorder, Delta Storage Pool Deficiency, Hermasky-Publak Syndrome, and Chediak-Higashi Syndrome.

In other embodiments, the compositions and methods of the invention relate to inhibitors of NPP4. The compositions and methods of the invention include compositions and methods for treating or preventing disorders and diseases where a decreased activity or level of NPP4 is desirable. In various embodiments, the disorders and diseases where decreased activity or level of NPP4 is desirable which can be treated or prevented with the compositions and methods of the invention included diseases and disorders where the inhibition of coagulation is desirable, including, but not limited to, thrombosis, including thrombosis due to a genetic defect, venous thrombosis, deep vein thrombosis, portal vein thrombosis, renal vein thrombosis, jugular vein thrombosis, Budd-Chiari Syndrome, Paget-Schroetter Disease, cerebral venous sinus thrombosis, arterial thrombosis, coronary artery disease, peripheral vascular disease, stroke, and myocardial infarction.

Definitions

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

The term "abnormal" when used in the context of organisms, tissues, cells or components thereof, refers to those organisms, tissues, cells or components thereof that differ in at least one observable or detectable characteristic (e.g., age, treatment, time of day, etc.) from those organisms, tissues, cells or components thereof that display the "normal" (expected) respective characteristic. Characteristics which are normal or expected for one cell or tissue type, might be abnormal for a different cell or tissue type.

An "allele" refers to one specific form of a genetic sequence (such as a gene) within a cell, an individual or within a population, the specific form differing from other forms of the same gene in the sequence of at least one, and frequently more than one, variant sites within the sequence of the gene. The sequences at these variant sites that differ between different alleles are termed "variants," "polymorphisms," or "mutations."

As used herein, to "alleviate" or "treat" a disease means reducing the frequency or severity of at least one sign or symptom of a disease or disorder.

As used herein the terms "alteration," "defect," "variation," or "mutation," refers to a mutation in a gene in a cell that affects the function, activity, expression (transcription or translation) or conformation of the polypeptide that it encodes. Mutations encompassed by the present invention can be any mutation of a gene in a cell that results in the enhancement or disruption of the function, activity, expression or conformation of the encoded polypeptide, including the complete absence of expression of the encoded protein and can include, for example, missense and nonsense mutations, insertions, deletions, frameshifts and premature terminations. Without being so limited, mutations encompassed by the present invention may alter splicing the mRNA (splice site mutation) or cause a shift in the reading frame (frameshift).

The term "amplification" refers to the operation by which the number of copies of a target nucleotide sequence present in a sample is multiplied.

The term "antibody," as used herein, refers to an immunoglobulin molecule which is able to specifically bind to a specific epitope on an antigen. Antibodies can be intact immunoglobulins derived from natural sources or from recombinant sources and can be immunoreactive portions of intact immunoglobulins. The antibodies in the present invention may exist in a variety of forms including, for example, polyclonal antibodies, monoclonal antibodies, intracellular antibodies ("intrabodies"), Fv, Fab and F(ab)2, as well as single chain antibodies (scFv), heavy chain antibodies, such as camelid antibodies, synthetic antibodies, chimeric antibodies, and a humanized antibodies (Harlow et al., 1999, Using Antibodies: A Laboratory Manual, Cold Spring Harbor Laboratory Press, NY; Harlow et al., 1989, Antibodies: A Laboratory Manual, Cold Spring Harbor, N.Y.; Houston et al., 1988, Proc. Natl. Acad. Sci. USA 85:5879-5883; Bird et al., 1988, Science 242:423-426).

An "antibody heavy chain," as used herein, refers to the larger of the two types of polypeptide chains present in all antibody molecules in their naturally occurring conformations.

An "antibody light chain," as used herein, refers to the smaller of the two types of polypeptide chains present in all antibody molecules in their naturally occurring conformations. κ and λ light chains refer to the two major antibody light chain isotypes.

By the term "synthetic antibody" as used herein, is meant an antibody which is generated using recombinant DNA technology, such as, for example, an antibody expressed by a bacteriophage as described herein. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using synthetic DNA or amino acid sequence technology which is available and well known in the art.

As used herein, an "immunoassay" refers to any binding assay that uses an antibody capable of binding specifically to a target molecule to detect and quantify the target molecule.

By the term "specifically binds," as used herein with respect to an antibody, is meant an antibody which recognizes a specific antigen, but does not substantially recognize or bind other molecules in a sample. For example, an antibody that specifically binds to an antigen from one species may also bind to that antigen from one or more species. But, such cross-species reactivity does not itself alter the classification of an antibody as specific. In another example, an antibody that specifically binds to an antigen may also bind to different allelic forms of the antigen. However, such cross reactivity does not itself alter the classification of an antibody as specific. In some instances, the terms "specific binding" or "specifically binding," can be used in reference to the interaction of an antibody, a protein, or a peptide with a second chemical species, to mean that the interaction is dependent upon the presence of a particular structure (e.g., an antigenic determinant or epitope) on the chemical species; for example, an antibody recognizes and binds to a specific protein structure rather than to proteins generally. If an antibody is specific for epitope "A", the presence of a molecule containing epitope A (or free, unlabeled A), in a reaction containing labeled "A" and the antibody, will reduce the amount of labeled A bound to the antibody.

By the term "applicator," as the term is used herein, is meant any device including, but not limited to, a hypodermic syringe, a pipette, an iontophoresis device, a patch, and the like, for administering the compositions of the invention to a subject.

The term "coding sequence," as used herein, means a sequence of a nucleic acid or its complement, or a part thereof, that can be transcribed and/or translated to produce the mRNA and/or the polypeptide or a fragment thereof. Coding sequences include exons in a genomic DNA or immature primary RNA transcripts, which are joined together by the cell's biochemical machinery to provide a mature mRNA. The anti-sense strand is the complement of such a nucleic acid, and the coding sequence can be deduced therefrom. In contrast, the term "non-coding sequence," as used herein, means a sequence of a nucleic acid or its complement, or a part thereof, that is not translated into amino acid in vivo, or where tRNA does not interact to place or attempt to place an amino acid. Non-coding sequences include both intron sequences in genomic DNA or immature primary RNA transcripts, and gene-associated sequences such as promoters, enhancers, silencers, and the like.

As used herein, the terms "complementary" or "complementarity" are used in reference to polynucleotides (i.e., a sequence of nucleotides) related by the base-pairing rules. For example, the sequence "A-G-T," is complementary to the sequence "T-C-A." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods that depend upon binding between nucleic acids.

A "disease" is a state of health of an animal wherein the animal cannot maintain homeostasis, and wherein if the disease is not ameliorated then the animal's health continues to deteriorate. In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

An "effective amount" as used herein, means an amount which provides a therapeutic or prophylactic benefit.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

As used herein, the term "fragment," as applied to a nucleic acid, refers to a subsequence of a larger nucleic acid. A "fragment" of a nucleic acid can be at least about 15 nucleotides in length; for example, at least about 50 nucleotides to about 100 nucleotides; at least about 100 to about 500 nucleotides, at least about 500 to about 1000 nucleotides; at least about 1000 nucleotides to about 1500 nucleotides; about 1500 nucleotides to about 2500 nucleotides; or about 2500 nucleotides (and any integer value in between). As used herein, the term "fragment," as applied to a protein or peptide, refers to a subsequence of a larger protein or peptide. A "fragment" of a protein or peptide can be at least about 20 amino acids in length; for example, at least about 50 amino acids in length; at least about 100 amino acids in length; at least about 200 amino acids in length; at least about 300 amino acids in length; or at least about 400 amino acids in length (and any integer value in between).

The term "gene" refers to a nucleic acid (e.g., DNA) sequence that includes coding sequences necessary for the production of a polypeptide, precursor, or RNA (e.g., mRNA). The polypeptide may be encoded by a full length coding sequence or by any portion of the coding sequence so long as the desired activity or functional property (e.g., enzymatic activity, ligand binding, signal transduction, immunogenicity, etc.) of the full-length or fragment is retained. The term also encompasses the coding region of a structural gene and the sequences located adjacent to the coding region on both the 5' and 3' ends for a distance of about 2 kb or more on either end such that the gene corresponds to the length of the full-length mRNA and 5' regulatory sequences which influence the transcriptional properties of the gene. Sequences located 5' of the coding region and present on the mRNA are referred to as 5'-untranslated sequences. The 5'-untranslated sequences usually contain the regulatory sequences. Sequences located 3' or downstream of the coding region and present on the mRNA are referred to as 3'-untranslated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene that are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

"Homologous" refers to the sequence similarity or sequence identity between two polypeptides or between two nucleic acid molecules. When a position in both of the two compared sequences is occupied by the same base or amino acid monomer subunit, e.g., if a position in each of two DNA molecules is occupied by adenine, then the molecules are homologous at that position. The percent of homology between two sequences is a function of the number of matching or homologous positions shared by the two sequences divided by the number of positions compared X 100. For example, if 6 of 10 of the positions in two sequences are matched or homologous then the two sequences are 60% homologous. By way of example, the DNA sequences ATTGCC and TATGGC share 50% homology. Generally, a comparison is made when two sequences are aligned to give maximum homology.

As used herein, the term "hybridization" is used in reference to the pairing of complementary nucleic acids. Hybridization and the strength of hybridization (i.e., the strength of the association between the nucleic acids) is impacted by such factors as the degree of complementarity between the nucleic acids, stringency of the conditions involved, the $T_m$ of the formed hybrid, and the G:C ratio within the nucleic acids. A single molecule that contains pairing of complementary nucleic acids within its structure is said to be "self-hybridized." A single DNA molecule with internal complementarity could assume a variety of secondary structures including loops, kinks or, for long stretches of base pairs, coils.

The term "immunoglobulin" or "Ig," as used herein is defined as a class of proteins, which function as antibodies. Antibodies expressed by B cells are sometimes referred to as the BCR (B cell receptor) or antigen receptor. The five members included in this class of proteins are IgA, IgG, IgM, IgD, and IgE. IgA is the primary antibody that is present in body secretions, such as saliva, tears, breast milk, gastrointestinal secretions and mucus secretions of the respiratory and genitourinary tracts. IgG is the most common circulating antibody. IgM is the main immunoglobulin produced in the primary immune response in most subjects. It is the most efficient immunoglobulin in agglutination, complement fixation, and other antibody responses, and is important in defense against bacteria and viruses. IgD is the immunoglobulin that has no known antibody function, but may serve as an antigen receptor. IgE is the immunoglobulin that mediates immediate hypersensitivity by causing release of mediators from mast cells and basophils upon exposure to allergen.

"Instructional material," as that term is used herein, includes a publication, a recording, a diagram, or any other medium of expression which can be used to communicate the usefulness of the nucleic acid, peptide, and/or compound of the invention in the kit for identifying or alleviating or treating the various diseases or disorders recited herein. Optionally, or alternately, the instructional material may describe one or more methods of identifying or alleviating the diseases or disorders in a cell or a tissue of a subject. The instructional material of the kit may, for example, be affixed to a container that contains the nucleic acid, polypeptide, and/or compound of the invention or be shipped together with a container that contains the nucleic acid, polypeptide, and/or compound. Alternatively, the instructional material may be shipped separately from the container with the intention that the recipient uses the instructional material and the compound cooperatively.

"Isolated" means altered or removed from the natural state. For example, a nucleic acid or a polypeptide naturally present in a living animal is not "isolated," but the same nucleic acid or polypeptide partially or completely separated from the coexisting materials of its natural state is "isolated." An isolated nucleic acid or protein can exist in substantially purified form, or can exist in a non-native environment such as, for example, a host cell.

An "isolated nucleic acid" refers to a nucleic acid segment or fragment which has been separated from sequences which flank it in a naturally occurring state, e.g., a DNA fragment which has been removed from the sequences which are normally adjacent to the fragment, e.g., the sequences adjacent to the fragment in a genome in which it naturally occurs. The term also applies to nucleic acids which have been substantially purified from other components which naturally accompany the nucleic acid, e.g., RNA or DNA or proteins, which naturally accompany it in the cell. The term therefore includes, for example, a recombinant DNA which is incorporated into a vector, into an autonomously replicating plasmid or virus, or into the genomic DNA of a prokaryote or eukaryote, or which exists as a separate molecule (e.g., as a cDNA or a genomic or cDNA fragment produced by PCR or restriction enzyme digestion) independent of other sequences. It also includes a recombinant DNA which is part of a hybrid gene encoding additional polypeptide sequence.

The term "label" when used herein refers to a detectable compound or composition that is conjugated directly or indirectly to a probe to generate a "labeled" probe. The label may be detectable by itself (e.g. radioisotope labels or fluorescent labels) or, in the case of an enzymatic label, may catalyze chemical alteration of a substrate compound or composition that is detectable (e.g., avidin-biotin). In some instances, primers can be labeled to detect a PCR product.

The terms "microarray" and "array" refers broadly to "DNA microarrays," "DNA chip(s)," "protein microarrays" and "protein chip(s)" and encompasses all art-recognized solid supports, and all art-recognized methods for affixing nucleic acid, peptide, and polypeptide molecules thereto. Preferred arrays typically comprise a plurality of different nucleic acid or peptide probes that are coupled to a surface of a substrate in different, known locations. These arrays, also described as "microarrays" or colloquially "chips" have been generally described in the art, for example, U.S. Pat. Nos. 5,143,854, 5,445,934, 5,744,305, 5,677,195, 5,800, 992, 6,040,193, 5,424,186 and Fodor et al., 1991, Science, 251:767-777, each of which is incorporated by reference in its entirety for all purposes. Arrays may generally be produced using a variety of techniques, such as mechanical synthesis methods or light directed synthesis methods that incorporate a combination of photolithographic methods and solid phase synthesis methods. Techniques for the synthesis of these arrays using mechanical synthesis methods are described in, e.g., U.S. Pat. Nos. 5,384,261, and 6,040,193, which are incorporated herein by reference in their entirety for all purposes. Although a planar array surface is preferred, the array may be fabricated on a surface of virtually any shape or even a multiplicity of surfaces. Arrays may be nucleic acids on beads, gels, polymeric surfaces, fibers such as fiber optics, glass or any other appropriate substrate. (See U.S. Pat. Nos. 5,770,358, 5,789,162, 5,708,153, 6,040,193 and 5,800,992, which are hereby incorporated by reference in their entirety for all purposes.) Arrays may be packaged in such a manner as to allow for diagnostic use or can be an all-inclusive device; e.g., U.S. Pat. Nos. 5,856,174 and 5,922,591 incorporated in their entirety by reference for all purposes. Arrays are commercially available from, for example, Affymetrix (Santa Clara, Calif.) and Applied Biosystems (Foster City, Calif.), and are directed to a variety of purposes, including genotyping, diagnostics, mutation analysis, marker expression, and gene expression monitoring for a variety of eukaryotic and prokaryotic organisms. The number of probes on a solid support may be varied by changing the size of the individual features. In one embodiment the feature size is 20 by 25 microns square, in other embodiments features may be, for example, 8 by 8, 5 by 5 or 3 by 3 microns square, resulting in about 2,600,000, 6,600,000 or 18,000,000 individual probe features.

By the term "modulating," as used herein, is meant mediating a detectable increase or decrease in the activity and/or level of a mRNA, polypeptide, or a response in a subject compared with the activity and/or level of a mRNA, polypeptide or a response in the subject in the absence of a treatment or compound, and/or compared with the activity and/or level of a mRNA, polypeptide, or a response in an otherwise identical but untreated subject. The term encompasses activating, inhibiting and/or otherwise affecting a native signal or response thereby mediating a beneficial therapeutic response in a subject, preferably, a human.

A "mutation," as used herein, refers to a change in nucleic acid or polypeptide sequence relative to a reference sequence (which is preferably a naturally-occurring normal or "wild-type" sequence), and includes translocations, deletions, insertions, and substitutions/point mutations. A "mutant" as used herein, refers to either a nucleic acid or protein comprising a mutation.

A "nucleic acid" refers to a polynucleotide and includes poly-ribonucleotides and poly-deoxyribonucleotides. Nucleic acids according to the present invention may include any polymer or oligomer of pyrimidine and purine bases, preferably cytosine, thymine, and uracil, and adenine and guanine, respectively. (See Albert L. Lehninger, Principles of Biochemistry, at 793-800 (Worth Pub. 1982) which is herein incorporated in its entirety for all purposes). Indeed, the present invention contemplates any deoxyribonucleotide, ribonucleotide or peptide nucleic acid component, and any chemical variants thereof, such as methylated, hydroxymethylated or glucosylated forms of these bases, and the like. The polymers or oligomers may be heterogeneous or homogeneous in composition, and may be isolated from naturally occurring sources or may be artificially or synthetically produced. In addition, the nucleic acids may be DNA or RNA, or a mixture thereof, and may exist permanently or transitionally in single-stranded or double-stranded form, including homoduplex, heteroduplex, and hybrid states.

An "oligonucleotide" or "polynucleotide" is a nucleic acid ranging from at least 2, preferably at least 8, 15 or 25 nucleotides in length, but may be up to 50, 100, 1000, or 5000 nucleotides long or a compound that specifically hybridizes to a polynucleotide. Polynucleotides include sequences of deoxyribonucleic acid (DNA) or ribonucleic acid (RNA) or mimetics thereof which may be isolated from natural sources, recombinantly produced or artificially synthesized. A further example of a polynucleotide of the present invention may be a peptide nucleic acid (PNA). (See U.S. Pat. No. 6,156,501 which is hereby incorporated by reference in its entirety.) The invention also encompasses situations in which there is a nontraditional base pairing such as Hoogsteen base pairing which has been identified in certain tRNA molecules and postulated to exist in a triple helix. "Polynucleotide" and "oligonucleotide" are used interchangeably in this disclosure. It will be understood that when a nucleotide sequence is represented herein by a DNA sequence (e.g., A, T, G, and C), this also includes the corresponding RNA sequence (e.g., A, U, G, C) in which "U" replaces "T".

The terms "patient," "subject," "individual," and the like are used interchangeably herein, and refer to any animal, or cells thereof whether in vitro or in situ, amenable to the methods described herein. In certain non-limiting embodiments, the patient, subject or individual is a human.

As used herein, the term "polymerase chain reaction" ("PCR") refers to the method of K. B. Mullis (U.S. Pat. Nos. 4,683,195 4,683,202, and 4,965,188, hereby incorporated by reference) for increasing the concentration of a segment of a target sequence in a mixture of genomic DNA without cloning or purification. This process for amplifying the target sequence consists of introducing a large excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured and the primers then annealed to their complementary sequences within the target molecule. Following annealing, the primers are extended with a polymerase so as to form a new pair of complementary strands. The steps of denaturation, primer annealing and polymerase extension can be repeated many times (i.e., denaturation, annealing and extension constitute one "cycle"; there can be numerous "cycles") to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to as the "polymerase chain reaction" (hereinafter "PCR"). Because the desired amplified segments of the target sequence become the predominant sequences (in terms of concentration) in the mixture, they are said to be "PCR amplified". As used herein, the terms "PCR product," "PCR fragment," "amplification product" or "amplicon" refer to the resultant mixture of compounds after two or more cycles of the PCR steps of denaturation, annealing and extension are complete. These terms encompass the case where there has been amplification of one or more segments of one or more target sequences.

As used herein, the term "probe" refers to an oligonucleotide (i.e., a sequence of nucleotides), whether occurring naturally as in a purified restriction digest or produced synthetically, recombinantly or by PCR amplification, that is capable of hybridizing to another oligonucleotide of interest. A probe may be single-stranded or double-stranded. Probes are useful in the detection, identification and isolation of particular gene sequences.

The term "perfect match," "match," "perfect match probe" or "perfect match control" refers to a nucleic acid that has a sequence that is perfectly complementary to a particular target sequence. The nucleic acid is typically perfectly complementary to a portion (subsequence) of the target sequence. A perfect match (PM) probe can be a "test probe," a "normalization control" probe, an expression level control probe and the like. A perfect match control or perfect match is, however, distinguished from a "mismatch" or "mismatch probe." The term "mismatch," "mismatch control" or "mismatch probe" refers to a nucleic acid whose sequence is not perfectly complementary to a particular target sequence. As a non-limiting example, for each mismatch (MM) control in a high-density probe array there typically exists a corresponding perfect match (PM) probe that is perfectly complementary to the same particular target sequence. The mismatch may comprise one or more bases. While the mismatch(es) may be located anywhere in the mismatch probe, terminal mismatches are less desirable because a terminal mismatch is less likely to prevent hybridization of the target sequence. In a particularly preferred embodiment, the mismatch is located at or near the center of the probe such that the mismatch is most likely to destabilize the duplex with the target sequence under the test hybridization conditions.

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

As used herein, "polynucleotide" includes cDNA, RNA, DNA/RNA hybrid, antisense RNA, ribozyme, genomic DNA, synthetic forms, and mixed polymers, both sense and antisense strands, and may be chemically or biochemically modified to contain non-natural or derivatized, synthetic, or semi-synthetic nucleotide bases. Also, contemplated are alterations of a wild type or synthetic gene, including but not limited to deletion, insertion, substitution of one or more nucleotides, or fusion to other polynucleotide sequences.

To "prevent" a disease or disorder as the term is used herein, means to reduce the likelihood of at least one sign or symptom of a disease or disorder being experienced by a subject.

The term "primer" refers to an oligonucleotide capable of acting as a point of initiation of synthesis along a complementary strand when conditions are suitable for synthesis of a primer extension product. The synthesizing conditions include the presence of four different deoxyribonucleotide triphosphates and at least one polymerization-inducing agent such as reverse transcriptase or DNA polymerase. These are present in a suitable buffer, which may include constituents which are co-factors or which affect conditions such as pH and the like at various suitable temperatures. A primer is preferably a single strand sequence, such that amplification efficiency is optimized, but double stranded sequences can be utilized.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

The term "reaction mixture" or "PCR reaction mixture" or "master mix" or "master mixture" refers to an aqueous solution of constituents in a PCR reaction that can be constant across different reactions. An exemplary PCR reaction mixture includes buffer, a mixture of deoxyribonucleoside triphosphates, primers, probes, and DNA polymerase. Generally, template RNA or DNA is the variable in a PCR.

"Sample" or "biological sample" as used herein means a biological material isolated from a subject. The biological sample may contain any biological material suitable for detecting a mRNA, polypeptide or other marker of a physiologic or pathologic process in a subject, and may comprise fluid, tissue, cellular and/or non-cellular material obtained from the individual.

As used herein, "substantially purified" refers to being essentially free of other components. For example, a substantially purified polypeptide is a polypeptide which has been separated from other components with which it is normally associated in its naturally occurring state.

The term "target" as used herein refers to a molecule that has an affinity for a given probe. Targets may be naturally-occurring or man-made molecules. Also, they can be employed in their unaltered state or as aggregates with other species. Targets may be attached, covalently or noncovalently, to a binding member, either directly or via a specific binding substance. Targets are sometimes referred to in the art as anti-probes. As the term targets is used herein, no difference in meaning is intended.

As used herein, the terms "therapy" or "therapeutic regimen" refer to those activities taken to alleviate or alter a disorder or disease state, e.g., a course of treatment intended to reduce or eliminate at least one sign or symptom of a disease or disorder using pharmacological, surgical, dietary and/or other techniques. A therapeutic regimen may include a prescribed dosage of one or more compounds or surgery. Therapies will most often be beneficial and reduce or eliminate at least one sign or symptom of the disorder or disease state, but in some instances the effect of a therapy will have non-desirable or side-effects. The effect of therapy will also be impacted by the physiological state of the subject, e.g., age, gender, genetics, weight, other disease conditions, etc.

The term "therapeutically effective amount" refers to the amount of the subject compound that will elicit the biological or medical response of a tissue, system, or subject that is being sought by the researcher, veterinarian, medical doctor or other clinician. The term "therapeutically effective amount" includes that amount of a compound that, when administered, is sufficient to prevent development of, or alleviate to some extent, one or more of the signs or symptoms of the disorder or disease being treated. The therapeutically effective amount will vary depending on the compound, the disease and its severity and the age, weight, etc., of the subject to be treated.

To "treat" a disease or disorder as the term is used herein, means to reduce the frequency or severity of at least one sign or symptom of a disease or disorder experienced by a subject.

As used herein, the term "wild-type" refers to a gene or gene product isolated from a naturally occurring source. A wild-type gene is that which is most frequently observed in a population and is thus arbitrarily designed the "normal" or "wild-type" form of the gene. In contrast, the term "modified" or "mutant" refers to a gene or gene product that displays modifications in sequence and/or functional properties (i.e., altered characteristics) when compared to the wild-type gene or gene product. It is noted that naturally occurring mutants can be isolated; these are identified by the fact that they have altered characteristics (including altered nucleic acid sequences) when compared to the wild-type gene or gene product.

DESCRIPTION

In some embodiments, the invention relates to compositions and methods for increasing the activity of NPP4 to promote platelet degranulation, platelet aggregation and coagulation, while in other embodiments, the invention relates to compositions and method for decreasing the activity of NPP4 to diminish platelet degranulation, platelet aggregation and coagulation.

Thus, in some embodiments, the compositions of the invention relate to activators of NPP4. The methods of the invention include methods of treating or preventing disorders and diseases where an increased activity or level of NPP4 is desirable. In various embodiments, the disorders and diseases where an increased activity or level of NPP4 is desirable which can be treated or prevented with the compositions and methods of the invention include bleeding, coagulopathy, including coagulopathy due to a genetic defect, NSAID-associated coagulopathy, thrombocytopenia, Glanzmann's thrombasthenia, Bernard-Soulier syndrome, Von Willebrand's Disease, Hemophilia, Platelet Storage Pool Deficiency, Gray Platelet Syndrome, Quebec Platelet Disorder, Delta Storage Pool Deficiency, Hermasky-Publak Syndrome, and Chediak-Higashi Syndrome.

While in other embodiments, the compositions of the invention relate to inhibitors of NPP4. The methods of the invention include methods of treating or preventing disorders and diseases where a decreased activity or level of NPP4 is desirable. In various embodiments, the disorders and diseases where a decreased activity or level of NPP4 is desirable which can be treated or prevented with the compositions and methods of the invention include, coagulation, thrombosis, including thrombosis due to a genetic defect, venous thrombosis, deep vein thrombosis, portal vein thrombosis, renal vein thrombosis, jugular vein thrombosis, Budd-Chiari Syndrome, Paget-Schroetter Disease, cerebral venous sinus thrombosis, arterial thrombosis, coronary artery disease, peripheral vascular disease, stroke, and myocardial infarction.

Therapeutic Activator Compositions and Methods

In various embodiments, the present invention includes NPP4 activator compositions and methods of increasing coagulation in a subject, a tissue, or an organ in need thereof. In various embodiments, the NPP4 activator compositions and methods of treatment of the invention increase the amount of NPP4 polypeptide, the amount of NPP4 mRNA, the amount of NPP4 enzymatic activity, the amount of NPP4 substrate binding activity, or a combination thereof. In various embodiments, the diseases and disorders where in increase in coagulation may improve therapeutic outcome include, but are not limited to, bleeding, coagulopathy, including coagulopathy due to a genetic defect, NSAID-associated coagulopathy, thrombocytopenia, Glanzmann's thrombasthenia, Bernard-Soulier syndrome, Von Willebrand's Disease, Hemophilia, Platelet Storage Pool Deficiency, Gray Platelet Syndrome, Quebec Platelet Disorder, Delta Storage Pool Deficiency, Hermasky-Publak Syndrome, and Chediak-Higashi Syndrome.

It will be understood by one skilled in the art, based upon the disclosure provided herein, that an increase in the level of NPP4 encompasses the increase in NPP4 expression, including transcription, translation, or both. The skilled artisan will also appreciate, once armed with the teachings of the present invention, that an increase in the level of NPP4 includes an increase in NPP4 activity (e.g., enzymatic activity, substrate binding activity, etc.). Thus, increasing the level or activity of NPP4 includes, but is not limited to, increasing the amount of NPP4 polypeptide, and increasing transcription, translation, or both, of a nucleic acid encoding NPP4; and it also includes increasing any activity of an NPP4 polypeptide as well. The NPP4 activator compositions and methods of the invention can selectively activate NPP4, or can activate both NPP4 and another molecule.

Thus, the present invention relates to the prevention and treatment of a disease or disorder by administration of an NPP4 polypeptide, a recombinant NPP4 polypeptide, an active NPP4 polypeptide fragment, or an activator of NPP4 expression or activity. In one embodiment, the NPP4 polypeptide is soluble. In another embodiment, the NPP4 polypeptide is a recombinant NPP4 polypeptide. In one embodiment, the NPP4 polypeptide fragment includes an NPP4 polypeptide that lacks the NPP4 transmembrane domain. In a specific embodiment, the NPP4 polypeptide fragment includes amino acid residues 1-407 of SEQ ID NO:1.

It is understood by one skilled in the art, that an increase in the level of NPP4 encompasses an increase in the amount of NPP4 (e.g., by administration of NPP4 or a fragment thereof, by increasing NPP4 protein expression, etc.). Additionally, the skilled artisan would appreciate, that an increase in the level of NPP4 includes an increase in NPP4 activity. Thus, increasing the level or activity of NPP4 includes, but is not limited to, the administration of NPP4 or a fragment thereof, as well as increasing transcription, translation, or both, of a nucleic acid encoding NPP4; and it also includes increasing any activity of NPP4 as well.

The increased level or activity of NPP4 can be assessed using a wide variety of methods, including those disclosed herein, as well as methods well-known in the art or to be developed in the future. That is, the routineer would appreciate, based upon the disclosure provided herein, that increasing the level or activity of NPP4 can be readily assessed using methods that assess the level of a nucleic acid encoding NPP4 (e.g., mRNA), the level of NPP4 polypeptide, and/or the level of NPP4 activity in a biological sample obtained from a subject.

One skilled in the art, based upon the disclosure provided herein, would understand that the invention is useful in subjects who, in whole (e.g., systemically) or in part (e.g., locally, tissue, organ), are being or will be, treated for bleeding. In one embodiment, the invention is useful in treating or preventing bleeding. The skilled artisan will appreciate, based upon the teachings provided herein, that the diseases and disorders treatable by the compositions and methods described herein encompass any disease or disorder where in an increase in coagulation will promote a positive therapeutic outcome.

One of skill in the art will realize that in addition to activating NPP4 directly, diminishing the amount or activity of a molecule that itself diminishes the amount or activity of NPP4 can serve to increase the amount or activity of NPP4. Thus, an NPP4 activator can include, but should not be construed as being limited to, a chemical compound, a protein, a peptidomemetic, an antibody, a ribozyme, and an antisense nucleic acid molecule. One of skill in the art would readily appreciate, based on the disclosure provided herein, that an NPP4 activator encompasses a chemical compound that increases the level, enzymatic activity, or substrate binding activity of NPP4. Additionally, an NPP4 activator encompasses a chemically modified compound, and derivatives, as is well known to one of skill in the chemical arts.

It will be understood by one skilled in the art, based upon the disclosure provided herein, that an increase in the level of NPP4 encompasses the increase in NPP4 expression, including transcription, translation, or both. The skilled artisan will also appreciate, once armed with the teachings of the present invention, that an increase in the level of NPP4 includes an increase in NPP4 activity (e.g., enzymatic activity, substrate binding activity, etc.). Thus, increasing the level or activity of NPP4 includes, but is not limited to, increasing the amount of NPP4 polypeptide, increasing transcription, translation, or both, of a nucleic acid encoding NPP4; and it also includes increasing any activity of an NPP4 polypeptide as well. The NPP4 activator compositions and methods of the invention can selectively activate NPP4, or can activate both NPP4 and another molecule. Thus, the present invention relates to administration of an NPP4 polypeptide, a recombinant NPP4 polypeptide, an active NPP4 polypeptide fragment, or an activator of NPP4 expression or activity. In one embodiment, the NPP4 polypeptide is soluble. In another embodiment, the NPP4 polypeptide is a recombinant NPP4 polypeptide. In one embodiment, the NPP4 polypeptide fragment includes an NPP4 polypeptide that lacks the NPP4 transmembrane domain. In a specific embodiment, the NPP4 polypeptide fragment includes amino acid residues 1-407 of SEQ ID NO:1.

Further, one of skill in the art would, when equipped with this disclosure and the methods exemplified herein, appreciate that an NPP4 activator includes such activators as discovered in the future, as can be identified by well-known criteria in the art of pharmacology, such as the physiological results of activation of NPP4 as described in detail herein and/or as known in the art. Therefore, the present invention is not limited in any way to any particular NPP4 activator as exemplified or disclosed herein; rather, the invention encompasses those activators that would be understood by the routineer to be useful as are known in the art and as are discovered in the future.

Further methods of identifying and producing an NPP4 activator are well known to those of ordinary skill in the art, including, but not limited, obtaining an activator from a naturally occurring source (e.g., *Streptomyces* sp., *Pseudomonas* sp., *Stylotella aurantium*, etc.). Alternatively, an NPP4 activator can be synthesized chemically. Further, the routineer would appreciate, based upon the teachings provided herein, that an NPP4 activator can be obtained from a recombinant organism. Compositions and methods for chemically synthesizing NPP4 activators and for obtaining them from natural sources are well known in the art and are described in the art.

One of skill in the art will appreciate that an activator can be administered as a small molecule chemical, a protein, a nucleic acid construct encoding a protein, or combinations thereof. Numerous vectors and other compositions and methods are well known for administering a protein or a nucleic acid construct encoding a protein to cells or tissues. Therefore, the invention includes a method of administering a protein or a nucleic acid encoding an protein that is an activator of NPP4. (Sambrook et al., 2012, Molecular Cloning: A Laboratory Manual, Cold Spring Harbor Laboratory, New York; Ausubel et al., 1997, Current Protocols in Molecular Biology, John Wiley & Sons, New York).

One of skill in the art will realize that diminishing the amount or activity of a molecule that itself diminishes the amount or activity of NPP4 can serve to increase the amount or activity of NPP4. Antisense oligonucleotides are DNA or RNA molecules that are complementary to some portion of a mRNA molecule. When present in a cell, antisense oligonucleotides hybridize to an existing mRNA molecule and inhibit translation into a gene product. Inhibiting the expression of a gene using an antisense oligonucleotide is well known in the art (Marcus-Sekura, 1988, Anal. Biochem. 172:289), as are methods of expressing an antisense oligonucleotide in a cell (Inoue, U.S. Pat. No. 5,190,931). The methods of the invention include the use of antisense oligonucleotide to diminish the amount of a molecule that causes a decrease in the amount or activity NPP4, thereby increasing the amount or activity of NPP4. Contemplated in the present invention are antisense oligonucleotides that are synthesized and provided to the cell by way of methods well known to those of ordinary skill in the art. As an example, an antisense oligonucleotide can be synthesized to be between about 10 and about 100, more preferably between about 15 and about 50 nucleotides long. The synthesis of nucleic acid molecules is well known in the art, as is the synthesis of modified antisense oligonucleotides to improve biological activity in comparison to unmodified antisense oligonucleotides (Tullis, 1991, U.S. Pat. No. 5,023,243).

Similarly, the expression of a gene may be inhibited by the hybridization of an antisense molecule to a promoter or other regulatory element of a gene, thereby affecting the transcription of the gene. Methods for the identification of a promoter or other regulatory element that interacts with a gene of interest are well known in the art, and include such methods as the yeast two hybrid system (Bartel and Fields, eds., In: The Yeast Two Hybrid System, Oxford University Press, Cary, N.C.).

Alternatively, inhibition of a gene expressing a protein that diminishes the level or activity of NPP4 can be accomplished through the use of a ribozyme. Using ribozymes for inhibiting gene expression is well known to those of skill in the art (see, e.g., Cech et al., 1992, J. Biol. Chem. 267: 17479; Hampel et al., 1989, Biochemistry 28: 4929; Altman et al., U.S. Pat. No. 5,168,053). Ribozymes are catalytic RNA molecules with the ability to cleave other single-stranded RNA molecules. Ribozymes are known to be sequence specific, and can therefore be modified to recognize a specific nucleotide sequence (Cech, 1988, J. Amer. Med. Assn. 260:3030), allowing the selective cleavage of specific mRNA molecules. Given the nucleotide sequence of the molecule, one of ordinary skill in the art could synthesize an antisense oligonucleotide or ribozyme without undue experimentation, provided with the disclosure and references incorporated herein.

One of skill in the art will appreciate that an NPP4 activator, NPP4 polypeptide, a recombinant NPP4 polypeptide, or an active NPP4 polypeptide fragment can be administered singly or in any combination thereof. One of skill in the art will also appreciate administration can be acute (e.g., over a short period of time, such as a day, a week or a month) or chronic (e.g., over a long period of time, such as several months or a year or more). Further, an NPP4 polypeptide, a recombinant NPP4 polypeptide, or an active NPP4 polypeptide fragment can be administered singly or in any combination thereof in a temporal sense, in that they may be administered simultaneously, before, and/or after each other. One of ordinary skill in the art will appreciate, based on the disclosure provided herein, that an NPP4 polypeptide, a recombinant NPP4 polypeptide, or an active NPP4 polypeptide fragment can be used to promote coagulation, and that an activator can be used alone or in any combination with another NPP4 polypeptide, recombinant NPP4 polypeptide, active NPP4 polypeptide fragment, or NPP4 activator to effect a therapeutic result.

It will be appreciated by one of skill in the art, when armed with the present disclosure including the methods detailed herein, that the invention is not limited to treatment of a disease or disorder once is established. Particularly, the symptoms of the disease or disorder need not have manifested to the point of detriment to the subject; indeed, the disease or disorder need not be detected in a subject before treatment is administered. That is, significant pathology from disease or disorder does not have to occur before the present invention may provide benefit. Therefore, the present invention, as described more fully herein, includes a method for preventing diseases and disorders in a subject, in that an NPP4 molecule, or an NPP4 activator, as discussed elsewhere herein, can be administered to a subject prior to the onset of the disease or disorder, thereby preventing the disease or disorder from developing.

One of skill in the art, when armed with the disclosure herein, would appreciate that the prevention of a disease or disorder in a subject encompasses administering to a subject an NPP4 polypeptide, a recombinant NPP4 polypeptide, an active NPP4 polypeptide fragment, or NPP4 activator as a preventative measure against a disease or disorder. In one embodiment, the NPP4 polypeptide is soluble. In another embodiment, the NPP4 polypeptide is a recombinant NPP4 polypeptide. In one embodiment, the NPP4 polypeptide fragment includes an NPP4 polypeptide that lacks the NPP4 transmembrane domain. In a specific embodiment, the NPP4 polypeptide fragment includes amino acid residues 1-407 of SEQ ID NO:1. As more fully discussed elsewhere herein, methods of increasing the level or activity of an NPP4 encompass a wide plethora of techniques for increasing not only NPP4 activity, but also for increasing expression of a nucleic acid encoding NPP4. Additionally, as disclosed elsewhere herein, one skilled in the art would understand, once armed with the teaching provided herein, that the present invention encompasses a method of preventing a wide variety of diseases or disorders where increased expression and/or activity of NPP4 mediates, treats or prevents a disease or disorder. Further, the invention encompasses treatment or prevention of such diseases or disorders discovered in the future.

The invention encompasses administration of an NPP4 polypeptide, a recombinant NPP4 polypeptide, an active NPP4 polypeptide fragment, or an NPP4 activator to practice the methods of the invention; the skilled artisan would understand, based on the disclosure provided herein, how to formulate and administer the appropriate NPP4 polypeptide, recombinant NPP4 polypeptide, active NPP4 polypeptide fragment, or NPP4 activator to a subject. However, the present invention is not limited to any particular method of administration or treatment regimen. This is especially true where it would be appreciated by one skilled in the art, equipped with the disclosure provided herein, including the reduction to practice using an art-recognized model of ischemia-reperfusion injury, that methods of administering an NPP4 polypeptide, a recombinant NPP4 polypeptide, an active NPP4 polypeptide fragment, or NPP4 activator can be determined by one of skill in the pharmacological arts.

As used herein, the term "pharmaceutically-acceptable carrier" means a chemical composition with which an appropriate NPP4 modulator may be combined and which, following the combination, can be used to administer the appropriate NPP4 modulator thereof, to a subject.

Therapeutic Inhibitor Compositions and Methods

In various embodiments, the present invention includes NPP4 inhibitor compositions and methods of treating or preventing a disease or disorder where a diminished activity or level of NPP4 is desired. Non-limiting examples of diseases or disorders where a diminished activity or level of NPP4 is desired which can be treated compositions and methods of the invention include coagulation, thrombosis, including thrombosis due to a genetic defect, venous thrombosis, deep vein thrombosis, portal vein thrombosis, renal vein thrombosis, jugular vein thrombosis, Budd-Chiari Syndrome, Paget-Schroetter Disease, cerebral venous sinus thrombosis, arterial thrombosis, coronary artery disease, peripheral vascular disease, stroke, and myocardial infarction. In various embodiments, the NPP4 inhibitor compositions and methods of treatment of the invention diminish the amount of NPP4 polypeptide, the amount of NPP4 mRNA, the amount of NPP4 enzymatic activity, the amount of NPP4 substrate binding activity, or a combination thereof.

It will be understood by one skilled in the art, based upon the disclosure provided herein, that a decrease in the level of NPP4 encompasses the decrease in NPP4 expression, including transcription, translation, or both. The skilled artisan will also appreciate, once armed with the teachings of the present invention, that a decrease in the level of NPP4 includes a decrease in NPP4 activity (e.g., enzymatic activity, substrate binding activity, etc.). Thus, decreasing the level or activity of NPP4 includes, but is not limited to, decreasing transcription, translation, or both, of a nucleic acid encoding NPP4; and it also includes decreasing any activity of an NPP4 polypeptide as well. The NPP4 inhibitor compositions and methods of the invention can selectively inhibit NPP4, or can inhibit both NPP4 and another molecule.

Inhibition of NPP4 can be assessed using a wide variety of methods, including those disclosed herein, as well as methods known in the art or to be developed in the future. That is, the routineer would appreciate, based upon the disclosure provided herein, that decreasing the level or activity of NPP4 can be readily assessed using methods that assess the level of a nucleic acid encoding NPP4 (e.g., mRNA), the level of an NPP4 polypeptide present in a biological sample, the level of NPP4 activity (e.g., enzymatic activity, substrate binding activity, etc.), or combinations thereof.

One skilled in the art, based upon the disclosure provided herein, would understand that the invention is useful in diminishing coagulation in a subject in need thereof, whether or not the subject also being treated with other medication or therapy. Further, the skilled artisan would further appreciate, based upon the teachings provided herein, that the disease or disorders treatable by the compositions and methods described herein encompass any disease or disorder where NPP4 plays a role and where diminished coagulation with promote a positive therapeutic outcome.

The NPP4 inhibitor compositions and methods of the invention that decrease the level or activity (e.g., enzymatic activity, substrate binding activity, etc.) of NPP4 include, but should not be construed as being limited to, a chemical compound, a protein, a peptide, a peptidomemetic, an antibody, a ribozyme, a small molecule chemical compound, an antisense nucleic acid molecule (e.g., siRNA, miRNA, etc.), or combinations thereof. One of skill in the art would readily appreciate, based on the disclosure provided herein, that an NPP4 inhibitor composition encompasses a chemical compound that decreases the level or activity of NPP4. Additionally, an NPP4 inhibitor composition encompasses a chemically modified compound, and derivatives, as is well known to one of skill in the chemical arts.

The NPP4 inhibitor compositions and methods of the invention that decrease the level or activity (e.g., enzymatic activity, substrate binding activity, etc.) of NPP4 include antibodies. The antibodies of the invention include a variety of forms of antibodies including, for example, polyclonal antibodies, monoclonal antibodies, intracellular antibodies ("intrabodies"), Fv, Fab and F(ab)2, single chain antibodies (scFv), heavy chain antibodies (such as camelid antibodies), synthetic antibodies, chimeric antibodies, and a humanized antibodies. In one embodiment, the antibody of the invention is an antibody that specifically binds to NPP4.

Further, one of skill in the art, when equipped with this disclosure and the methods exemplified herein, would appreciate that an NPP4 inhibitor composition includes such inhibitors as discovered in the future, as can be identified by well-known criteria in the art of pharmacology, such as the physiological results of inhibition of NPP4 as described in detail herein and/or as known in the art. Therefore, the present invention is not limited in any way to any particular NPP4 inhibitor composition as exemplified or disclosed herein; rather, the invention encompasses those inhibitor compositions that would be understood by the routineer to be useful as are known in the art and as are discovered in the future.

Further methods of identifying and producing NPP4 inhibitor compositions are well known to those of ordinary skill in the art, including, but not limited, obtaining an inhibitor from a naturally occurring source (e.g., *Streptomyces* sp., *Pseudomonas* sp., *Stylotella aurantium*, etc.). Alternatively, an NPP4 inhibitor can be synthesized chemically. Further, the routineer would appreciate, based upon the teachings provided herein, that an NPP4 inhibitor composition can be obtained from a recombinant organism. Compositions and methods for chemically synthesizing NPP4 inhibitors and for obtaining them from natural sources are well known in the art and are described in the art.

One of skill in the art will appreciate that an inhibitor can be administered as a small molecule chemical, a protein, an antibody, a nucleic acid construct encoding a protein, an antisense nucleic acid, a nucleic acid construct encoding an antisense nucleic acid, or combinations thereof. Numerous vectors and other compositions and methods are well known for administering a protein or a nucleic acid construct encoding a protein to cells or tissues. Therefore, the invention includes a method of administering a protein or a nucleic acid encoding a protein that is an inhibitor of NPP4. (Sambrook et al., 2012, Molecular Cloning: A Laboratory Manual, Cold Spring Harbor Laboratory, New York; Ausubel et al., 1997, Current Protocols in Molecular Biology, John Wiley & Sons, New York).

One of skill in the art will realize that diminishing the amount or activity of a molecule that itself increases the amount or activity of NPP4 can serve in the compositions and methods of the present invention to decrease the amount or activity of NPP4.

Antisense oligonucleotides are DNA or RNA molecules that are complementary to some portion of an RNA molecule. When present in a cell, antisense oligonucleotides hybridize to an existing RNA molecule and inhibit translation into a gene product. Inhibiting the expression of a gene using an antisense oligonucleotide is well known in the art (Marcus-Sekura, 1988, Anal. Biochem. 172:289), as are methods of expressing an antisense oligonucleotide in a cell (Inoue, U.S. Pat. No. 5,190,931). The methods of the invention include the use of an antisense oligonucleotide to diminish the amount of NPP4, or to diminish the amount of a molecule that causes an increase in the amount or activity of NPP4, thereby decreasing the amount or activity of NPP4.

Contemplated in the present invention are antisense oligonucleotides that are synthesized and provided to the cell by way of methods well known to those of ordinary skill in the art. As an example, an antisense oligonucleotide can be synthesized to be between about 10 and about 100, more preferably between about 15 and about 50 nucleotides long. The synthesis of nucleic acid molecules is well known in the art, as is the synthesis of modified antisense oligonucleotides to improve biological activity in comparison to unmodified antisense oligonucleotides (Tullis, 1991, U.S. Pat. No. 5,023,243).

Similarly, the expression of a gene may be inhibited by the hybridization of an antisense molecule to a promoter or other regulatory element of a gene, thereby affecting the transcription of the gene. Methods for the identification of a promoter or other regulatory element that interacts with a gene of interest are well known in the art, and include such methods as the yeast two hybrid system (Bartel and Fields, eds., In: The Yeast Two Hybrid System, Oxford University Press, Cary, N.C.).

Alternatively, inhibition of a gene expressing NPP4, or of a gene expressing a protein that increases the level or activity of NPP4, can be accomplished through the use of a ribozyme. Using ribozymes for inhibiting gene expression is well known to those of skill in the art (see, e.g., Cech et al., 1992, J. Biol. Chem. 267:17479; Hampel et al., 1989, Biochemistry 28: 4929; Altman et al., U.S. Pat. No. 5,168,053). Ribozymes are catalytic RNA molecules with the ability to cleave other single-stranded RNA molecules. Ribozymes are known to be sequence specific, and can therefore be modified to recognize a specific nucleotide sequence (Cech, 1988, J. Amer. Med. Assn. 260:3030), allowing the selective cleavage of specific mRNA molecules. Given the nucleotide sequence of the molecule, one of ordinary skill in the art could synthesize an antisense oligonucleotide or ribozyme without undue experimentation, provided with the disclosure and references incorporated herein.

One of skill in the art will appreciate that inhibitors of NPP4 can be administered acutely (e.g., over a short period of time, such as a day, a week or a month) or chronically (e.g., over a long period of time, such as several months or a year or more). One of skill in the art will appreciate that inhibitors of NPP4 can be administered singly or in any combination with other agents. Further, NPP4 inhibitors can be administered singly or in any combination in a temporal sense, in that they may be administered concurrently, or before, and/or after each other. One of ordinary skill in the art will appreciate, based on the disclosure provided herein, that NPP4 inhibitor compositions can be used to treat or prevent a disease or disorder in a subject in need thereof, and that an inhibitor composition can be used alone or in any combination with another inhibitor to effect a therapeutic result.

In various embodiments, any of the inhibitors of NPP4 of the invention described herein can be administered alone or in combination with other inhibitors of other molecules associated with coagulation.

It will be appreciated by one of skill in the art, when armed with the present disclosure including the methods detailed herein, that the invention is not limited to treatment of a disease or disorder that is already established. Particularly, the disease or disorder need not have manifested to the point of detriment to the subject; indeed, the disease or disorder need not be detected in a subject before treatment is administered. That is, significant disease or disorder does not have to occur before the present invention may provide benefit. Therefore, the present invention includes a method for preventing a disease or disorder in a subject, in that an NPP4 inhibitor composition, as discussed previously elsewhere herein, can be administered to a subject prior to the onset of the disease or disorder, thereby preventing the disease or disorder from developing. The preventive methods described herein also include the treatment of a subject that is in remission for the prevention of a recurrence of a disease or disorder.

One of skill in the art, when armed with the disclosure herein, would appreciate that the prevention of a disease or disorder encompasses administering to a subject an NPP4 inhibitor composition as a preventative measure against the disease or disorder. As more fully discussed elsewhere herein, methods of decreasing the level or activity of NPP4 encompass a wide plethora of techniques for decreasing not only NPP4 activity, but also for decreasing expression of a nucleic acid encoding NPP4, including either a decrease in transcription, a decrease in translation, or both.

Additionally, as disclosed elsewhere herein, one skilled in the art would understand, once armed with the teaching provided herein, that the present invention encompasses a method of preventing a wide variety of diseases, disorders and pathologies where a decrease in expression and/or activity of NPP4 mediates, treats or prevents the disease, disorder or pathology. Methods for assessing whether a disease relates to the levels or activity of NPP4 are known in the art. Further, the invention encompasses treatment or prevention of such diseases discovered in the future.

The invention encompasses administration of an inhibitor of NPP4 to practice the methods of the invention; the skilled artisan would understand, based on the disclosure provided herein, how to formulate and administer the appropriate NPP4 inhibitor to a subject. However, the present invention is not limited to any particular method of administration or treatment regimen.

Methods of Identifying an NPP4 Activator or NPP4 Inhibitor

The current invention relates to a method of identifying a compound that modulates the level of NPP4, the enzymatic activity of NPP4, the substrate binding activity of NPP4, or a combination thereof. In some embodiments, the method of identifying of the invention identifies an NPP4 inhibitor compound that decreases the level of NPP4, the enzymatic activity of NPP4, the substrate binding activity of NPP4, or a combination thereof. In other embodiments, the method of identifying of the invention identifies an NPP4 activator compound that increases the level of NPP4, the enzymatic activity of NPP4, the substrate binding activity of NPP4, or a combination thereof.

The invention relates to a method for screening test compounds to identify a modulator compound by its ability to modulate (i.e., increase or decrease) the level of NPP4, the enzymatic activity of NPP4, the substrate binding activity of NPP4, or a combination thereof, by measuring the level of NPP4, the enzymatic activity of NPP4, the substrate binding activity of NPP4, or a combination thereof, in the presence and absence of the test compound. Other methods, as well as variation of the methods disclosed herein will be apparent from the description of this invention. In various embodiments, the test compound concentration in the screening assay can be fixed or varied. A single test compound, or a plurality of test compounds, can be tested at one time. Suitable test compounds that may be used include, but are not limited to, proteins, nucleic acids, antisense nucleic acids, small molecules, antibodies and peptides.

In one embodiment, the invention comprises a method of identifying a test compound as a modulator of NPP4. Generally, the method of identifying a test compound as a modulator of NPP4 includes the steps of determining the level of NPP4 in the presence of a test compound, determining the level of NPP4 in the absence of the test compound, and comparing the level of NPP4 in the presence of the test compound with the level of NPP4 in the absence of the test compound. Thus, in some embodiments, the test compound is identified as a modulator of NPP4 when the level of the at least one of NPP4 in the presence of the test compound is different than level of NPP4 in the absence of the test compound. In one embodiment, when the level of NPP4 is higher in the presence of the test compound, the test compound is identified as an activator. In another embodiment, when the level of NPP4 is lower in the presence of the test compound, the test compound is identified as an inhibitor.

The test compounds can be obtained using any of the numerous approaches in combinatorial library methods known in the art, including: biological libraries; spatially addressable parallel solid phase or solution phase libraries; synthetic library methods requiring deconvolution; the "one-bead one-compound" library method; and synthetic library methods using affinity chromatography selection. The biological library approach is limited to peptide libraries, while the other four approaches are applicable to peptide, non-peptide oligomer or small molecule libraries of compounds (Lam et al., 1997, Anticancer Drug Des. 12:45).

Examples of methods for the synthesis of molecular libraries can be found in the art, for example, in: DeWitt et al., 1993, Proc. Natl. Acad. USA 90:6909; Erb et al., 1994, Proc. Natl. Acad. Sci. USA 91:11422; Zuckermann et al., 1994, J. Med. Chem. 37:2678; Cho et al., 1993, Science 261:1303; Carrell et al., 1994, Angew. Chem. Int. Ed. Engl. 33:2059; Carell et al., 1994, Angew. Chem. Int. Ed. Engl. 33:2061; and Gallop et al., 1994, J. Med. Chem. 37:1233.

Libraries of compounds may be presented in solution (e.g., Houghten, 1992, Biotechniques 13:412-421), or on beads (Lam, 1991, Nature 354:82-84), chips (Fodor, 1993, Nature 364:555-556), bacteria (Ladner U.S. Pat. No. 5,223,409), spores (Ladner U.S. Pat. No. '409), plasmids (Cull et al., 1992, Proc. Natl. Acad. Sci. USA 89:1865-1869) or on phage (Scott and Smith, 1990, Science 249:386-390; Devlin, 1990, Science 249:404-406; Cwirla et al., 1990, Proc. Natl. Acad. Sci. USA 87:6378-6382; Felici, 1991, J. Mol. Biol. 222:301-310; and Ladner supra).

In situations where "high-throughput" modalities are preferred, it is typical to that new chemical entities with useful properties are generated by identifying a chemical compound (called a "lead compound") with some desirable property or activity, creating variants of the lead compound, and evaluating the property and activity of those variant compounds.

In one embodiment, high throughput screening methods involve providing a library containing a large number of test compounds potentially having the desired activity. Such "combinatorial chemical libraries" are then screened in one or more assays, as described herein, to identify those library members (particular chemical species or subclasses) that display a desired characteristic activity. The compounds thus identified can serve as conventional "lead compounds" or can themselves be used as potential or actual therapeutics.

Kits

The present invention also pertains to kits useful in the methods of the invention. Such kits comprise various combinations of components useful in any of the methods described elsewhere herein, including for example, hybridization probes or primers (e.g., labeled probes or primers), antibodies, reagents for detection of labeled molecules, an NPP4 activator, an NPP4 inhibitor, materials for quantitatively analyzing NPP4 polypeptide or NPP4 nucleic acid, materials for assessing the activity of an NPP4 polypeptide or an NPP4 nucleic acid, and instructional material. For example, in one embodiment, the kit comprises components useful for the quantification of NPP4 nucleic acid in a biological sample. In another embodiment, the kit comprises components useful for the quantification of NPP4 polypeptide in a biological sample. In a further embodiment, the kit comprises components useful for the assessment of the activity (e.g., enzymatic activity, substrate binding activity, etc.) of an NPP4 polypeptide in a biological sample.

In a further embodiment, the kit comprises the components of an assay for monitoring the effectiveness of a treatment administered to a subject in need thereof, containing instructional material and the components for determining whether the level of NPP4 in a biological sample obtained from the subject is modulated during or after administration of the treatment. In various embodiments, to determine whether the level of NPP4 is modulated in a biological sample obtained from the subject, the level of NPP4 is compared with the level of at least one comparator control contained in the kit, such as a positive control, a negative control, a historical control, a historical norm, or the level of another reference molecule in the biological sample. In certain embodiments, the ratio of NPP4 and a reference molecule is determined to aid in the monitoring of the treatment.

Pharmaceutical Compositions

Compositions identified as modulators (i.e., activator or inhibitor) of NPP4 can be formulated and administered to a subject, as now described. For example, compositions identified as useful NPP4 inhibitors for the treatment and/or prevention of a disease or disorder can be formulated and administered to a subject, as now described. Further, compositions identified as useful NPP4 activators, including NPP4 polypeptides, recombinant NPP4 polypeptides, and active NPP4 polypeptide fragments, for the treatment and/or prevention of a disease or disorder can be formulated and administered to a subject, as now described.

The invention encompasses the preparation and use of pharmaceutical compositions comprising a composition useful for the treatment or prevention of a disease or disorder, disclosed herein as an active ingredient. Such a pharmaceutical composition may consist of the active ingredient alone, in a form suitable for administration to a subject, or the pharmaceutical composition may comprise the active ingredient and one or more pharmaceutically acceptable carriers, one or more additional ingredients, or some combination of these. The active ingredient may be present in the pharmaceutical composition in the form of a physiologically acceptable ester or salt, such as in combination with a physiologically acceptable cation or anion, as is well known in the art.

As used herein, the term "pharmaceutically-acceptable carrier" means a chemical composition with which an appropriate NPP4 modulator thereof, may be combined and which, following the combination, can be used to administer the appropriate NPP4 modulator thereof, to a subject.

The pharmaceutical compositions useful for practicing the invention may be administered to deliver a dose of between about 0.1 ng/kg/day and 100 mg/kg/day.

In various embodiments, the pharmaceutical compositions useful in the methods of the invention may be administered, by way of example, systemically, parenterally, or topically, such as, in oral formulations, inhaled formulations, including solid or aerosol, and by topical or other similar formulations. In addition to the appropriate therapeutic composition, such pharmaceutical compositions may contain pharmaceutically acceptable carriers and other ingredients known to enhance and facilitate drug administration. Other possible formulations, such as nanoparticles, liposomes, resealed erythrocytes, and immunologically based systems may also be used to administer an appropriate modulator thereof, according to the methods of the invention.

As used herein, the term "physiologically acceptable" ester or salt means an ester or salt form of the active ingredient which is compatible with any other ingredients of the pharmaceutical composition, which is not deleterious to the subject to which the composition is to be administered.

The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

Although the descriptions of pharmaceutical compositions provided herein are principally directed to pharmaceutical compositions which are suitable for ethical administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and perform such modification with merely ordinary, if any, experimentation.

Pharmaceutical compositions that are useful in the methods of the invention may be prepared, packaged, or sold in formulations suitable for oral, rectal, vaginal, parenteral, topical, pulmonary, intranasal, buccal, intravenous, ophthalmic, intrathecal and other known routes of administration. Other contemplated formulations include projected nanoparticles, liposomal preparations, resealed erythrocytes containing the active ingredient, and immunologically-based formulations.

A pharmaceutical composition of the invention may be prepared, packaged, or sold in bulk, as a single unit dose, or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject or a convenient fraction of such a dosage such as, for example, one-half or one-third of such a dosage.

The relative amounts of the active ingredient, the pharmaceutically acceptable carrier, and any additional ingredients in a pharmaceutical composition of the invention will vary, depending upon the identity, size, and condition of the subject treated and further depending upon the route by which the composition is to be administered. By way of example, the composition may comprise between 0.1% and 100% (w/w) active ingredient.

In addition to the active ingredient, a pharmaceutical composition of the invention may further comprise one or more additional pharmaceutically active agents.

Controlled- or sustained-release formulations of a pharmaceutical composition of the invention may be made using conventional technology.

A formulation of a pharmaceutical composition of the invention suitable for oral administration may be prepared, packaged, or sold in the form of a discrete solid dose unit including, but not limited to, a tablet, a hard or soft capsule, a cachet, a troche, or a lozenge, each containing a predetermined amount of the active ingredient. Other formulations suitable for oral administration include, but are not limited to, a powdered or granular formulation, an aqueous or oily suspension, an aqueous or oily solution, or an emulsion.

A tablet comprising the active ingredient may, for example, be made by compressing or molding the active ingredient, optionally with one or more additional ingredients. Compressed tablets may be prepared by compressing, in a suitable device, the active ingredient in a free-flowing form such as a powder or granular preparation, optionally mixed with one or more of a binder, a lubricant, an excipient, a surface active agent, and a dispersing agent. Molded tablets may be made by molding, in a suitable device, a mixture of the active ingredient, a pharmaceutically acceptable carrier, and at least sufficient liquid to moisten the mixture. Pharmaceutically acceptable excipients used in the manufacture of tablets include, but are not limited to, inert diluents, granulating and disintegrating agents, binding agents, and lubricating agents. Known dispersing agents include, but are not limited to, potato starch and sodium starch glycollate. Known surface active agents include, but are not limited to, sodium lauryl sulphate. Known diluents include, but are not limited to, calcium carbonate, sodium carbonate, lactose, microcrystalline cellulose, calcium phosphate, calcium hydrogen phosphate, and sodium phosphate. Known granulating and disintegrating agents include, but are not limited to, corn starch and alginic acid. Known binding agents include, but are not limited to, gelatin, acacia, pre-gelatinized maize starch, polyvinylpyrrolidone, and hydroxypropyl methylcellulose. Known lubricating agents include, but are not limited to, magnesium stearate, stearic acid, silica, and talc.

Tablets may be non-coated or they may be coated using known methods to achieve delayed disintegration in the gastrointestinal tract of a subject, thereby providing sustained release and absorption of the active ingredient. By way of example, a material such as glyceryl monostearate or glyceryl distearate may be used to coat tablets. Further by way of example, tablets may be coated using methods described in U.S. Pat. Nos. 4,256,108; 4,160,452; and U.S. Pat. No. 4,265,874 to form osmotically-controlled release tablets. Tablets may further comprise a sweetening agent, a flavoring agent, a coloring agent, a preservative, or some combination of these in order to provide pharmaceutically elegant and palatable preparation.

Hard capsules comprising the active ingredient may be made using a physiologically degradable composition, such as gelatin. Such hard capsules comprise the active ingredient, and may further comprise additional ingredients including, for example, an inert solid diluent such as calcium carbonate, calcium phosphate, or kaolin.

Soft gelatin capsules comprising the active ingredient may be made using a physiologically degradable composition, such as gelatin. Such soft capsules comprise the active ingredient, which may be mixed with water or an oil medium such as peanut oil, liquid paraffin, or olive oil.

Liquid formulations of a pharmaceutical composition of the invention which are suitable for oral administration may be prepared, packaged, and sold either in liquid form or in the form of a dry product intended for reconstitution with water or another suitable vehicle prior to use.

Liquid suspensions may be prepared using conventional methods to achieve suspension of the active ingredient in an aqueous or oily vehicle. Aqueous vehicles include, for example, water and isotonic saline. Oily vehicles include, for example, almond oil, oily esters, ethyl alcohol, vegetable oils such as arachis, olive, sesame, or coconut oil, fractionated vegetable oils, and mineral oils such as liquid paraffin. Liquid suspensions may further comprise one or more additional ingredients including, but not limited to, suspending agents, dispersing or wetting agents, emulsifying agents, demulcents, preservatives, buffers, salts, flavorings, coloring agents, and sweetening agents. Oily suspensions may further comprise a thickening agent.

Known suspending agents include, but are not limited to, sorbitol syrup, hydrogenated edible fats, sodium alginate, polyvinylpyrrolidone, gum tragacanth, gum acacia, and cellulose derivatives such as sodium carboxymethylcellulose, methylcellulose, and hydroxypropylmethylcellulose. Known dispersing or wetting agents include, but are not limited to, naturally-occurring phosphatides such as lecithin, condensation products of an alkylene oxide with a fatty acid, with a long chain aliphatic alcohol, with a partial ester derived from a fatty acid and a hexitol, or with a partial ester derived from a fatty acid and a hexitol anhydride (e.g. polyoxyethylene stearate, heptadecaethyleneoxycetanol, polyoxyethylene sorbitol monooleate, and polyoxyethylene sorbitan monooleate, respectively). Known emulsifying agents include, but are not limited to, lecithin and acacia. Known preservatives include, but are not limited to, methyl, ethyl, or n-propyl-para-hydroxybenzoates, ascorbic acid, and sorbic acid. Known sweetening agents include, for example, glycerol, propylene glycol, sorbitol, sucrose, and saccharin. Known thickening agents for oily suspensions include, for example, beeswax, hard paraffin, and cetyl alcohol.

Liquid solutions of the active ingredient in aqueous or oily solvents may be prepared in substantially the same manner as liquid suspensions, the primary difference being that the active ingredient is dissolved, rather than suspended in the solvent. Liquid solutions of the pharmaceutical composition of the invention may comprise each of the components described with regard to liquid suspensions, it being understood that suspending agents will not necessarily aid dissolution of the active ingredient in the solvent. Aqueous solvents include, for example, water and isotonic saline. Oily solvents include, for example, almond oil, oily esters, ethyl alcohol, vegetable oils such as arachis, olive, sesame, or coconut oil, fractionated vegetable oils, and mineral oils such as liquid paraffin.

Powdered and granular formulations of a pharmaceutical preparation of the invention may be prepared using known methods. Such formulations may be administered directly to a subject, used, for example, to form tablets, to fill capsules, or to prepare an aqueous or oily suspension or solution by addition of an aqueous or oily vehicle thereto. Each of these formulations may further comprise one or more of dispersing or wetting agent, a suspending agent, and a preservative. Additional excipients, such as fillers and sweetening, flavoring, or coloring agents, may also be included in these formulations.

A pharmaceutical composition of the invention may also be prepared, packaged, or sold in the form of oil-in-water emulsion or a water-in-oil emulsion. The oily phase may be a vegetable oil such as olive or arachis oil, a mineral oil such as liquid paraffin, or a combination of these. Such compositions may further comprise one or more emulsifying agents such as naturally occurring gums such as gum acacia or gum tragacanth, naturally-occurring phosphatides such as soybean or lecithin phosphatide, esters or partial esters derived from combinations of fatty acids and hexitol anhydrides such as sorbitan monooleate, and condensation products of such partial esters with ethylene oxide such as polyoxyethylene sorbitan monooleate. These emulsions may also contain additional ingredients including, for example, sweetening or flavoring agents.

Methods for impregnating or coating a material with a chemical composition are known in the art, and include, but are not limited to methods of depositing or binding a chemical composition onto a surface, methods of incorporating a chemical composition into the structure of a material during the synthesis of the material (i.e. such as with a physiologically degradable material), and methods of absorbing an aqueous or oily solution or suspension into an absorbent material, with or without subsequent drying.

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, cutaneous, subcutaneous, intraperitoneal, intravenous, intramuscular, intracisternal injection, and kidney dialytic infusion techniques.

Formulations of a pharmaceutical composition suitable for parenteral administration comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multi-dose containers containing a preservative. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In one embodiment of a formulation for parenteral administration, the active ingredient is provided in dry (i.e. powder or granular) form for reconstitution with a suitable vehicle (e.g., sterile pyrogen-free water) prior to parenteral administration of the reconstituted composition.

The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non-toxic parenterally-acceptable diluent or solvent, such as water or 1,3-butane diol, for example. Other acceptable diluents and solvents include, but are not limited to, Ringer's solution, isotonic sodium chloride solution, and fixed oils such as synthetic mono- or di-glycerides. Other parentally-administrable formulations which are useful include those which comprise the active ingredient in microcrystalline form, in a liposomal preparation, or as a component of a biodegradable polymer systems. Compositions for sustained release or implantation may comprise pharmaceutically acceptable polymeric or hydrophobic materials such as an emulsion, an ion exchange resin, a sparingly soluble polymer, or a sparingly soluble salt.

Formulations suitable for topical administration include, but are not limited to, liquid or semi-liquid preparations such as liniments, lotions, oil-in-water or water-in-oil emulsions such as creams, ointments or pastes, and solutions or suspensions. Topically-administrable formulations may, for example, comprise from about 1% to about 10% (w/w) active ingredient, although the concentration of the active ingredient may be as high as the solubility limit of the active ingredient in the solvent Formulations for topical administration may further comprise one or more of the additional ingredients described herein.

A pharmaceutical composition of the invention may be prepared, packaged, or sold in a formulation suitable for pulmonary administration via the buccal cavity. Such a formulation may comprise dry particles which comprise the active ingredient and which have a diameter in the range from about 0.5 to about 7 nanometers, and preferably from about 1 to about 6 nanometers. Such compositions are conveniently in the form of dry powders for administration using a device comprising a dry powder reservoir to which a stream of propellant may be directed to disperse the powder or using a self-propelling solvent/powder-dispensing container such as a device comprising the active ingredient dissolved or suspended in a low-boiling propellant in a sealed container. Preferably, such powders comprise particles wherein at least 98% of the particles by weight have a diameter greater than 0.5 nanometers and at least 95% of the particles by number have a diameter less than 7 nanometers. More preferably, at least 95% of the particles by weight have a diameter greater than 1 nanometer and at least 90% of the particles by number have a diameter less than 6 nanometers. Dry powder compositions preferably include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic or solid anionic surfactant or a solid diluent (preferably having a particle size of the same order as particles comprising the active ingredient).

Pharmaceutical compositions of the invention formulated for pulmonary delivery may also provide the active ingredient in the form of droplets of a solution or suspension. Such formulations may be prepared, packaged, or sold as aqueous or dilute alcoholic solutions or suspensions, optionally sterile, comprising the active ingredient, and may conveniently be administered using any nebulization or atomization device. Such formulations may further comprise one or more additional ingredients including, but not limited to, a flavoring agent such as saccharin sodium, a volatile oil, a buffering agent, a surface active agent, or a preservative such as methylhydroxybenzoate. The droplets provided by this route of administration preferably have an average diameter in the range from about 0.1 to about 200 nanometers.

The formulations described herein as being useful for pulmonary delivery are also useful for intranasal delivery of a pharmaceutical composition of the invention.

Another formulation suitable for intranasal administration is a coarse powder comprising the active ingredient and having an average particle from about 0.2 to 500 micrometers. Such a formulation is administered in the manner in which snuff is taken i.e. by rapid inhalation through the nasal passage from a container of the powder held close to the nares. Formulations suitable for nasal administration may, for example, comprise from about as little as 0.1% (w/w) and as much as 100% (w/w) of the active ingredient, and may further comprise one or more of the additional ingredients described herein.

A pharmaceutical composition of the invention may be prepared, packaged, or sold in a formulation suitable for buccal administration. Such formulations may, for example, be in the form of tablets or lozenges made using conventional methods, and may, for example, contain 0.1 to 20% (w/w) active ingredient, the balance comprising an orally dissolvable or degradable composition and, optionally, one or more of the additional ingredients described herein. Alternately, formulations suitable for buccal administration may comprise a powder or an aerosolized or atomized solution or suspension comprising the active ingredient. Such powdered, aerosolized, or aerosolized formulations, when dispersed, preferably have an average particle or droplet size in the range from about 0.1 to about 200 nanometers, and may further comprise one or more of the additional ingredients described herein.

A pharmaceutical composition of the invention may be prepared, packaged, or sold in a formulation suitable for ophthalmic administration. Such formulations may, for example, be in the form of eye drops including, for example, a 0.1-1.0% (w/w) solution or suspension of the active ingredient in an aqueous or oily liquid carrier. Such drops may further comprise buffering agents, salts, or one or more other of the additional ingredients described herein. Other opthalmically-administrable formulations which are useful include those which comprise the active ingredient in microcrystalline form or in a liposomal preparation.

As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" which may be included in the pharmaceutical compositions of the invention are known in the art and described, for example in Genaro, ed., 1985, Remington's Pharmaceutical Sciences, Mack Publishing Co., Easton, Pa., which is incorporated herein by reference.

Typically dosages of the compound of the invention which may be administered to an animal, preferably a human, range in amount from about 0.01 mg to 20 about 100 g per kilogram of body weight of the animal. While the precise dosage administered will vary depending upon any number of factors, including, but not limited to, the type of animal and type of disease state being treated, the age of the animal and the route of administration. Preferably, the dosage of the compound will vary from about 1 mg to about 100 mg per kilogram of body weight of the animal. More preferably, the dosage will vary from about 1 µg to about 1 g per kilogram of body weight of the animal. The compound can be administered to an animal as frequently as several times daily, or it can be administered less frequently, such as once a day, once a week, once every two weeks, once a month, or even less frequently, such as once every several months or even once a year or less. The frequency of the dose will be readily apparent to the skilled artisan and will depend upon any number of factors, such as, but not limited to, the type and severity of the disease being treated, the type and age of the animal, etc.

EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods. The following working examples therefore, specifically point out the preferred embodiments of the present invention, and are not to be construed as limiting in any way the remainder of the disclosure.

Example 1: NPP4 is a Procoagulant Enzyme on the Surface of Vascular Endothelium

Homology modeling revealed that the active sites of NPP4 and NPP1 to be quite similar, making NPP4 a candidate for Ap3A hydrolysis within blood vessels. NPP4 and NPP2 were assessed to investigate the role of the NPP family in hemostasis resulting from diadenosine polyphosphate metabolism. To define this role, purified soluble, recombinant extracellular domains of human NPP2 and NPP4 were expressed, their enzymatic activities with substrates Ap3A and Ap4A (also released by dense granules) were characterized, the intravascular location of NPP4 was confirmed by immunofluorescence, and turbidometric analysis was performed to directly determine the effects of NPPs on the aggregation of PRP. The results described herein demonstrate that NPP4 is a prothrombotic intravascular enzyme stimulating platelet aggregation through the sustained hydrolysis of Ap3A into ADP at the site of the nascent thrombus.

As the studies described herein demonstrate, NPP4, a previously uncharacterized member of the ectonucleotide pyrophosphatase/phosphodiesterase family, is localized on the vascular walls of blood vessels within the brain and activates platelet degranulation and aggregation at nM concentrations through the liberation of ADP from Ap3A (Albright et al., 2012, Blood doi: 10.1182/blood-2012-04-425215). Ap3A is a chemical stored in abundance in platelet dense granules that achieves ≈100 µM extracellular concentrations in the vicinity of platelet activation upon platelet degranulation. A search of the NCBI-GEO database also revealed NPP4 gene expression in a variety of human vascular endothelial cells. In contrast to previous reports, the experiments described herein provide no evidence that NPP2 is capable of hydrolyzing Ap3A either by steady state enzymatic studies (data not shown) or biological assays with platelet-rich plasma (FIG. 5C). In addition, the Michaelis constant of NPP4 binding to Ap3A found by the studies described herein is much weaker than previously reported for NPP1 and NPP3, 800 µM compared with 5-50 µM.

The data described herein demonstrate that NPP4 augments the platelet aggregation response to Ap3A, which is consistent with the explanation that the generation of ADP via hydrolysis of Ap3A is the mechanism by which this occurs. Additionally, it is demonstrated herein that NPP4/Ap3A-induced platelet aggregation is markedly inhibited by inclusion of an ADP receptor blockade (FIGS. 5A and 5B), providing further evidence for an ADP-dependent mechanism. Importantly, it is shown herein that these ADP-receptor inhibitors do not significantly impact NPP4 activity (FIG. 5C).

ADP stimulates platelet shape change, aggregation and secretion via activation of platelet surface receptors P2Y1 and P2Y12 that are coupled to intracellular G-proteins through which their signals are mediated. P2Y1 couples to Gq and mediates influx of Ca2+, platelet shape change and transient aggregation, while P2Y12 receptors couple to Gi family members and mediate inhibition of adenyl cyclase activity and augmentation of platelet aggregation. Optimal platelet aggregation requires activation of both ADP receptors. One consequence of exposure to ADP is the release of arachidonic acid (AA) from platelet membrane phospholipids. AA is subsequently converted to TXA2 via a pathway involving cyclooxygenase-1 (COX-1) and requiring the activation of both ADP receptors. This pathway is inhibited by aspirin, an effective antiplatelet agent, especially in the setting of cardiovascular disease. The studies described herein demonstrate that NPP4 augments ADP-mediated pathways of platelet aggregation, including that NPP4 is able to modulate the effects of COX-1 inhibition of platelet aggregation.

The results described herein are relevant to clinical approaches for both improving hemostasis and inhibiting thrombosis. First, NPP4 is a novel target for antithrombotic therapy as an adjunct to antiplatelet agents. Second, NPP4 enzyme replacement therapy to augment prolonged low-level ADP production and platelet aggregation at the site of vascular injury provides an alternative to platelet transfusions in bleeding patients with qualitative platelet dysfunction (such as, by way of non-limiting examples, due to NSAIDs or congenital storage pool disorders) by improving platelet function. Third, the demonstration that NPP4 is a vascular endothelial cell ectoenzyme with proaggregatory effects is consistent with the explanation that mutant forms or deficiencies of NPP4 are responsible for a mild bleeding diathesis in individuals with mucosal "platelet-type" bleeding manifestations for which no platelet or von Willebrand factor abnormalities can be identified.

The materials and methods employed in this experiment are now described.

Reagents

All reagents were the highest purity commercially available. Anti-NPP4 polyclonal antibody was obtained from Proteintech Group, Inc. (Chicago Ill.). The DyLight 549 goat anti-rabbit fluorescent antibody was obtained from Vector Labs (Burlingame, Calif.). Ap3A and Ap4A, p-Nitrophenyl 5'-thymidine monophosphate (pNP-TMP), and the ADP receptor antagonists, MRS 2179 (P2Y1) and MRS 2395 (P2Y12) were obtained from Sigma-Aldrich (St. Louis, Mo.). Substrates were freshly dissolved in assay buffers [absorbance assay—50 mM Tris pH 8.0, 140 mM NaCl, 5 mM KCl, 1 mM MgCl2 and 1 mM CaCl2— Malachite green screening assay—50 mM Tris pH 8.0, 140 mM NaCl, 5 mM KCl, 1 mM MgCl2 and 1 mM CaCl2, 0.1 mM ZnCl2—Platelet aggregation assay—50 mM Tris pH 8.0, 140 mM NaCl, 0.1 mM MgCl2 and 0.1 mM CaCl2, 0.1 mM ZnCl2] immediately before use. MRS 2179 was dissolved in water and MRS 2395 was dissolved in DMSO. Both receptor antagonist solutions were stored at −20° C. and thawed immediately before use in platelet aggregation assays.

Protein Expression

The extracellular domains of human NPP4 (NCBI accession AAH18054.1, residues 1-407), NPP4-T70A (a threonine to alanine point mutation in residue 70) and full length NPP2 (NCBI accession BC034961, residues 1-863) were cloned into a modified pFastbac HT vector possessing a TEV protease cleavage site followed by a C-terminus 9-HIS tag, and cloned and expressed in insect cells. Full-length NPP2 protein results in soluble, recombinant protein in the baculovirus cell culture media secondary to cleavage of the extracellular domain by furin (Jansen et al., 2005, J Cell Sci 118(Pt 14):3081-9). Only the extracellular domain of NPP4 (residues 1-407) was cloned and expressed in identical conditions, resulting in soluble, recombinant protein. The proteins were purified with a Ni-NTA column followed by TEV cleavage of the His tag. The TEV protease also contained a His-tag, allowing a second Ni-NTA column to remove the TEV and His fragment (Saunders et al., 2008, Molecular cancer therapeutics 7:3352-62).

NPP4 Amino Acid Sequence (SEQ ID NO: 1)
MKLLVILLFSGLITGFRSDSSSSLPPKLLLVSFDGFRADYLKNYEFPHLQ

NFIKEGVLVEHVKNVFITKTFPNHYSIVTGLYEESHGIVANSMYDAVTKK

HFSDSNDKDPFWWNEAVPIWVTNQLQENRSSAAAMWPGTDVPIHDTISSY

FMNYNSSVSFEERLNNITMWLNNSNPPVTFATLYWEEPDASGHKYGPEDK

ENMSRVLKKIDDLIGDLVQRLKMLGLWENLNVIITSDHGMTQCSQDRLIN

LDSCIDHSYYTLIDLSPVAAILPKINRTEVYNKLKNCSPHMNVYLKEDIP

NRFYYQHNDRIQPIILVADEGWTIVLNESSQKLGDHGYDNSLPSMHPFLA

AHGPAFHKGYKHSTINIVDIYPMMCHILGLKPHPNNGTFGHTKCLLVDQW

CINLPEAIAIVIGSLLVLTMLTCLIIIMQNRLSVPRPFSRLQLQEDDDDP

LIG

NPP2 Amino Acid Sequence (SEQ ID NO: 2)
MARRSSFQSCQIISLFTFAVGVNICLGFTAHRIKRAEGWEEGPPTVLSD

SPWTNISGSCKGRCFELQEAGPPDCRCDNLCKSYTSCCHDFDELCLKTAR

GWECTKDRCGEVRNEENACHCSEDCLARGDCCTNYQVVCKGESHWVDDDC

EEIKAAECPAGFVRPPLIIFSVDGFRASYMKKGSKVMPNIEKLRSCGTHS

PYMRPVYPTKTFPNLYTLATGLYPESHGIVGNSMYDPVFDATFHLRGREK

FNHRWWGGQPLWITATKQGVKAGTFFWSVVIPHERRILTILQWLTLPDHE

RPSVYAFYSEQPDFSGHKYGPFGPEMTNPLREIDKIVGQLMDGLKQLKLH

RCVNVIFVGDHGMEDVTCDRTEFLSNYLTNVDDITLVPGTLGRIRSKFSN

NAKYDPKAIIANLTCKKPDQHFKPYLKQHLPKRLHYANNRRIEDIHLLVE

RRWHVARKPLDVYKKPSGKCFFQGDHGFDNKVNSMQTVFVGYGPTFKYKT

KVPPFENIELYNVMCDLLGLKPAPNNGTHGSLNHLLRTNTFRPTMPEEVT

RPNYPGIMYLQSDFDLGCTCDDKVEPKNKLDELNKRLHTKGSTEERHLLY

GRPAVLYRTRYDILYHTDFESGYSEIFLMPLWTSYTVSKQAEVSSVPDHL

TSCVRPDVRVSPSFSQNCLAYKNDKQMSYGFLFPPYLSSSPEAKYDAFLV

TNMVPMYPAFKRVWNYFQRVLVKKYASERNGVNVISGPIFDYDYDGLHDT

EDKIKQYVEGSSIPVPTHYYSIITSCLDFTQPADKCDGPLSVSSFILPHR

PDNEESCNSSEDESKWVEELMKMHTARVRDIEHLTSLDFFRKTSRSYPEI

LTLKTYLHTYESEI

Immunofluorescence

Histologically normal human brain tissue was obtained from autopsy and was fixed in formalin for 6 weeks and then paraffin embedded. Paraffin embedded tissues were processed, sectioned, and stained with H&E by the Research Histology Laboratory at Yale. For immunofluorescent staining, paraffin tissues were sectioned at 5, deparaffinized, rehydrated, and heat induced epitope retrieval was performed in 1 mM citrate buffer, pH=6.0, for 20 minutes. Prior to staining, sections were washed with Tris Buffered Saline (TBS) and blocked for one hour at RT with 1% BSA, 3% normal goat serum, and 0.3% Triton X-100 in PBS. Thin sections were incubated with rabbit anti-NPP4 (Proteintech Group, Inc.) for 1 hour at RT, followed by goat anti-rabbit IgG conjugated to Dylight-549 (Vector Labs) for 30 minutes. The resulting staining was directly compared to negative controls prepared identically except omitting the goat anti-rabbit anti-NPP4 conjugated antibody.

Substrate Identification Screening

NPP4 nucleotide substrates were identified by directly detecting the free phosphate (Pi) product using malachite green (ADP substrate) or by a linked hydrolysis assay with alkaline phosphatase combined with malachite green (lipid substrates and nucleotide substrates without terminal $P_i$) to measure released $P_i$. 50 μM substrate $P_i$ equivalents (e.g. 25 μM ADP) were treated with 50 nM NPP4 for 1 hr 37 min (lipids) or 3 hr 15 min (all other substrates). For substrates without terminal phosphates, 10 units of calf intestinal alkaline phosphatase (M0290S, 10,000 units/mL, New England Biolabs, Ipswich, Mass.) was added for a final reaction volume of 50 μL. 100 μL of malachite green (Biomol Green™ Enzo Life Sciences, Plymouth Meeting, Pa.) was added to quench the reactions. The amount of phosphate released was measured by absorbance at 620 nm by a Biotek Synergy Mx plate reader (Winooski, Vt.) in 96-well plates (3679, Corning Inc., Corning, N.Y.) and compared against a phosphate standard curve. Reactions showing ≤6% phosphates released from the original substrate were considered to be inactive, while reactions showing 75 percent or more phosphates released from the original substrate were considered to be active. None of the reactions tested showed phosphate release between 6 and 75 percent.

Absorbance Change Assay for the Steady State Ap3A/Ap4A Cleavage by NPP4

The kinetics of the steady state Ap3A/Ap4A cleavage by NPP4 was measured from time courses of absorbance change at 259 nm using a UV spectrophotometer with a 0.1 cm optical path length cuvette or a stopped-flow device with a 0.2 cm optical path length cell. The enzymology reactions in 50 mM Tris pH 8.0, 140 mM NaCl, 5 mM KCl, 1 mM MgCl2 and 1 mM CaCl2 were started by addition of 1 µM NPP4 to varying concentrations of Ap3A/Ap4A (up to 800 µM) solution (UV spectrophotometer) or by rapid mixing of NPP4 and Ap3A/Ap4A (stopped-flow). The substrate concentrations higher than 800 µM have absorption too high to be measured by a UV spectrophotometer and stopped-flow, and were therefore measured by HPLC. HPLC assay indicates that the Ap3A hydrolysis products are AMP and ADP, while Ap4A hydrolysis products are AMP and ATP. Therefore, the rate of a product production or enzyme turnover measured by the absorption change assay can be calculated by the rate of absorption change $$\left(\frac{\Delta A}{\Delta t}\right)$$

according to the following formula;

$$r = \frac{\Delta[\text{product}]}{\Delta t} \Big/ [\text{enzyme}] = \frac{\Delta A}{\Delta t} \Big/ (15.4 \times 2 - \varepsilon_{Ap3A/Ap4A}) \Big/ \Delta l / [\text{enzyme}]$$

where $\Delta l$ is optical path length. The following absorption coefficients were used: Ap3A[19]: 25.75 mM$^{-1}$ cm$^{-1}$. Ap4A[20]: 25.4 mM$^{-1}$ cm$^{-1}$. AMP, ADP, and ATP[21]: 15.4 mM$^{-1}$ cm$^{-1}$.

ADP Receptor Inhibitor Assay for NPP4 Inhibition

The activity of NPP4 in the presence of the ADP receptor inhibitors was determined from the cleavage rate of pNP-TMP (20 mM) by NPP4 (5 nM) was measured at 405 nm in a UV spectrophotometer in the presence of 100 µM of either of the two ADP receptor antagonists or their appropriate control solutions (water for MRS 2179 and 10% DMSO for MRS 2395). All experimental conditions were measured in triplicate. Time courses of absorbance change were fitted to a linear function and the rate of cleavage was obtained using a p-nitrophenylate molar extinction coefficient of 18.5 mM$^{-1}$ cm$^{-1}$ as described (Saunders et al., 2008, Molecular cancer therapeutics 7:3352-62).

HPLC Assay

The HPLC protocol used to measure Ap3A/Ap4A cleavage by NPP4 and for product identification is modified from that of Stocchi et al. (1985, Anal Biochem 146:118-24). The reactions containing varying concentrations of Ap3A/Ap4A in the same buffer as in the absorbance change assay were started by addition of 0.2-1 µM NPP4 and quenched at various time points by equal volume of 3 M formic acid, or 0.5 N KOH and re-acidified by glacial acetic acid to pH 6. The quenched reaction solution was diluted systematically and loaded a HPLC system (Waters, Milford Mass.) and substrates and products were monitored by UV absorbance at 254 or 259 nm. Substrates and products were separated on a C18, 5 µm 250×4.6 mm HPLC column (Higgins Analytical, Mountain View, Calif.), using 15 mM ammonium acetate pH 6.0 solution, with a 0% to 10% (or 20%) methanol gradient. The products and substrate were quantified according to the integration of their correspondent peaks and the formula:

$$[\text{product/substrate}] = \frac{area_{product/substrate} / \varepsilon_{product/substrate}}{area_{product} / \varepsilon_{product} + area_{substrate} / \varepsilon_{substrate}} [\text{substrate}]_0$$

where [substrate]0 is the initial substrate concentration. The extinction coefficients of Ap3A, Ap4A, AMP, ADP and ATP used in the formula were the same as those used in absorption change assay. If monitoring at 254 nm, substrate and product standards run on the same day as the reactions were used to convert integrated product/substrate peak areas to concentrations.

Preparation of Human Platelets for Aggregometry

Whole blood from healthy voluntary donors was collected in accordance with an IRB-approved protocol into blue top vacutainer tubes containing 3.2% sodium citrate. Blood was centrifuged at 1000 RPM for 10 minutes at room temperature to collect platelet rich plasma (PRP). PRP in the supernatant was then transferred to fresh tubes, and the remainder of the specimen was centrifuged at 4000 RPM for 10 minutes to obtain platelet poor plasma (PPP). PRP was adjusted to a final platelet count of 250×106 platelets/mL with autologous PPP for use in aggregation studies. Potential donors were excluded if there was a history of a bleeding disorder or current anticoagulant use and donors were instructed to avoid NSAIDs for at least 7 days prior to donation. Approval for the human subjects involved in this research was sought and granted by the Committee for the Protection of Human Subjects, Dartmouth-Hitchcock Medical Center, where these studies were conducted in accordance with the Declaration of Helsinki.

Platelet Aggregometry

Light transmission (i.e., optical) and lumi aggregometry were performed on up to four samples from the same individual simultaneously with a Chrono-Log Model 700 Whole Blood/Optical Lumi Aggregometer (Chrono-Log Corporation, Havertown, Pa.) using procedures provided by the manufacturer that are briefly summarized here.

Light Transmission Aggregometry (LTA)

Platelet aggregation was determined by measuring the change in light transmittance of stirred PRP over time after addition of various agonists. Prior to each experiment the aggregometer was standardized to reflect 100% and 0% light transmittance with PPP and PRP, respectively, from the donor whose platelets were used in each specific experiment. 500 µL PRP was added to cuvettes containing a magnetic stir bar and allowed to pre-warm to 37° C. in the aggregometer wells for 3 minutes prior to initiating aggregation reactions which were then conducted at 37° C. Aggregation reactions were initiated by direct addition of agonists and/or enzymes to warmed, stirred PRP, and were monitored for an increase in light transmittance for 10 minutes. The increase in light transmittance is directly proportional to the amount of aggregation and is amplified and digitized into a computer (HP Compaq, Hewlett-Packard, Palo Alto, Calif.) with the AGGRO/LINK8 for Windows software (Chrono-Log Corporation, Havertown, Pa.) to generate aggregation curves. Aggregation curves originate from the top of the aggregation graphs and reflect the increase in percent light transmittance (and hence aggregation) over time. The platelet aggregometry experiments for all concentrations of MRS 2395 (including the 0 µM point) were conducted with the plasma adjusted to a final concentration of 10% DMSO to solubilize the inhibitor.

Lumi Aggregometry

In a subgroup of experiments, lumi aggregometry was used to assay the levels of extracellular ATP simultaneously with LTA. Lumi aggregometry measures ATP in the extracellular space over time using a sensitive luminescent assay employing firefly luciferin-luciferase (CHRONO-LUME™ reagent, Chrono-Log Corporation, Havertown, Pa.). ATP binds to luciferin-luciferase and generates light that is then amplified by a high-gain photomultiplier tube in the lumi aggregometer and is measured simultaneously with the optical change in light transmittance caused by platelet aggregation. In experiments in which lumi aggregometry was performed, 450 µL of PRP was transferred to cuvettes containing magnetic stir bars and allowed to pre-warm to 37° C. in the aggregometer wells for 3 minutes. 50 µL of CHRONOLUME™ reagent was added to each specimen and allowed to incubate for two additional minutes at 37° C. An ATP standard (Chrono-Log #387) is run for each individual test subject prior to adding agonists according to the instructions provided by the manufacturer. Reactions were initiated by the addition of agonists and/or enzymes to warmed PRP and CHRONOLUME™ reagent and were monitored for light generation. Light generation with the luciferin-luciferase is proportional to the amount of extracellular ATP present. In cases where the ATP originates from platelet dense granules, lumi aggregometry provides a method to assay the granule release reaction. Conversely, enzymatic reactions resulting in ATP can also be followed. Curves corresponding to light generation over time originate from the bottom of the aggregation graphs and reflect nM of ATP present in the extracellular space.

The results of this experimental example are now described.

NPP4 Tissue Localization by Immunofluorescence

Figure 1:
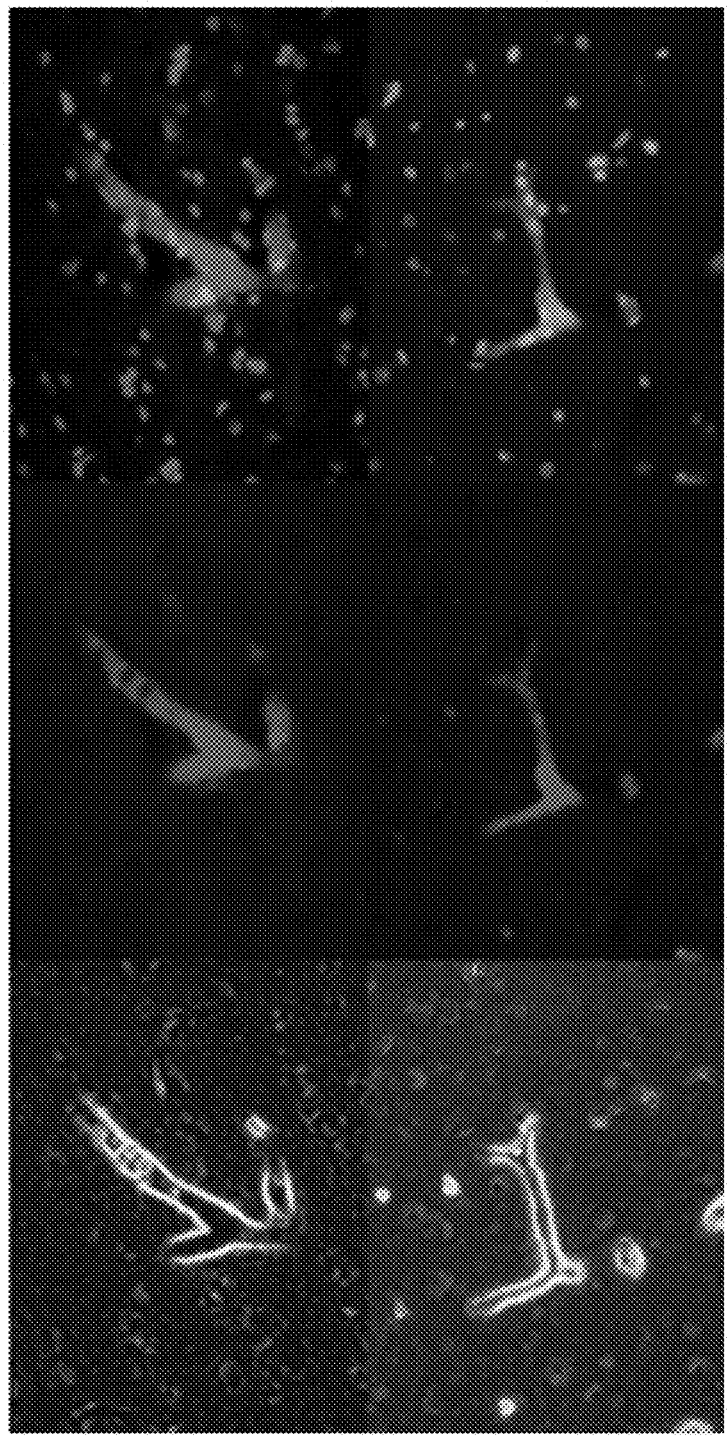
FIG. 1 depicts the results of experiments demonstrating that NPP4 is present on the vascular surfaces of human brain. To confirm the tissue localization of NPP4, adult human brain were stained with polyclonal rabbit anti-ENPP4 Ab (Proteintech Group), using Vector dylight 549 (red fluorescence Ab) to image. Strong staining was noted throughout the brain in all blood vessels, as demonstrated above in branched vessels above, two examples of which are displayed above. Left column—light contrast images of branched vessels. Middle column—red fluorescent channel of the identical field. Right Column—overlay of DAPI channel (blue) with NPP4 protein (red). Note the strong highlighting of NPP4 in branched blood vessels and cross sections of smaller vessels demonstrating NPP4 staining in the interior of the vessel.

To determine whether NPP4 is the Ap3A hydrolase present on vascular endothelial cell surfaces described by various research groups (Goldman et al., 1986, Circ Res 59:362-6; Ogilvie et al., 1989, Biochem J 259:97-103). The brain, a highly vascular human organ which accepts ~30% of cardiac output blood flow, was stained by immunofluorescence for NPP4 (FIG. 1). Immunofluorescence of NPP4 in brain reveals that NPP4 is enriched on blood vessel surfaces and localizes to vascular walls, as highlighting in numerous branched vessels in the brain parenchyma (FIG. 1). Sections of brain immunostained with secondary antibody alone failed to highlight branched vascular tissue with red fluorescence (data not shown), confirming that polyclonal rabbit anti-NPP4 antibody was responsible for the localization of the red fluorescent probe to the vascular walls.

NPP4 Hydrolysis of Diadenosine Polyphosphates

The extracellular domains of purified recombinant NPP4 and NPP2 were screened for substrate identification in enzyme assays using a linked assay in which alkaline phosphatase and either NPP4 or NPP2 were added to substrate, and free $P_i$ was detected via malachite green. The linked assay detected cleavage of Ap3A and Ap4A substrates by NPP4, but not by NPP2. In contrast to previously published reports (Vollmayer et al., 2003, Eur J Biochem 270:2971-8), no evidence of diadenosine polyphosphate hydrolysis with NPP2 was observed, either in the linked assay screen, or using a real time cleavage spectrophotometric assay (discussed elsewhere herein).

Figure 2:
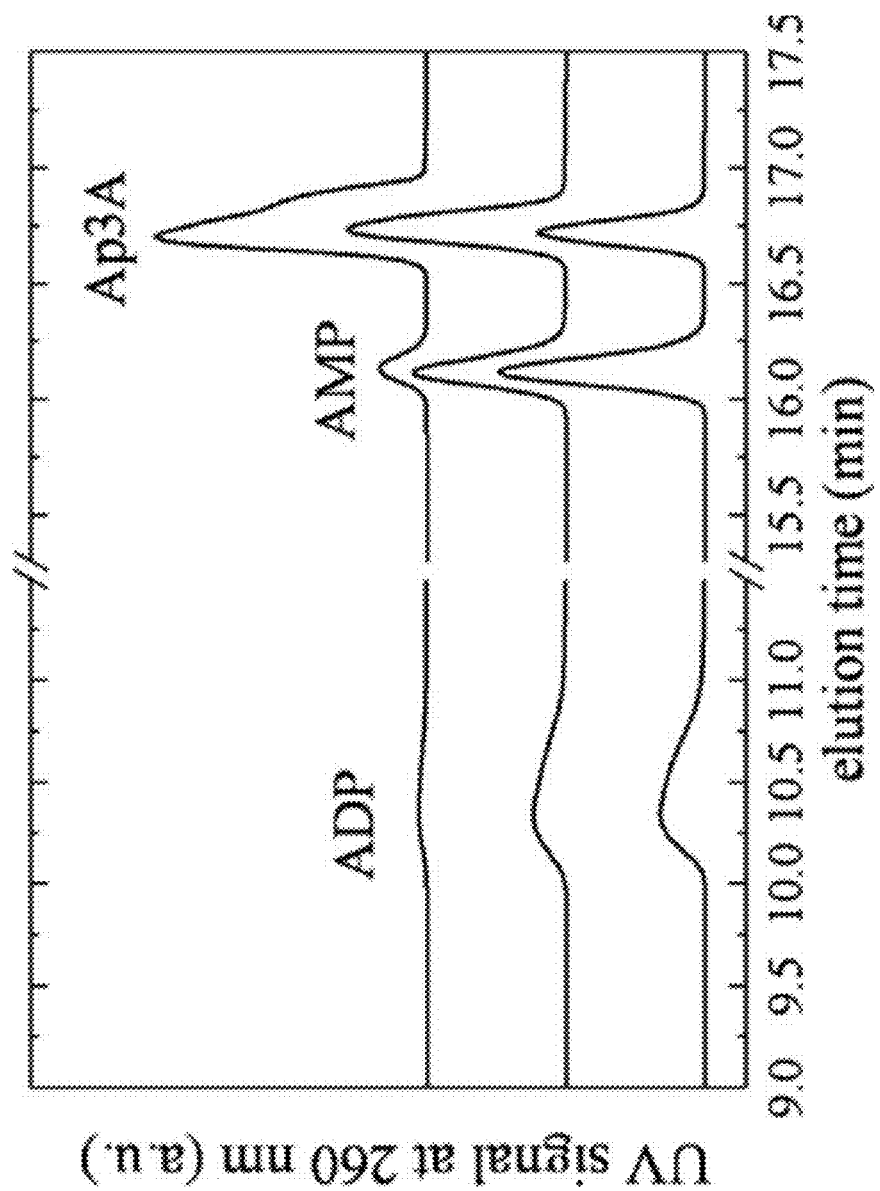
FIG. 2 depicts the results of experiments identifying Ap3A cleavage products by HPLC. Elution profile of NPP4-Ap3A reaction components. Top to bottom: reaction samples quenched at 2, 15, and 30 min. after mixing NPP4 with 800 μM Ap3A. The AMP/ADP product ratio determined from the integrated peak areas is ~1.1 at all times.
Figure 3:
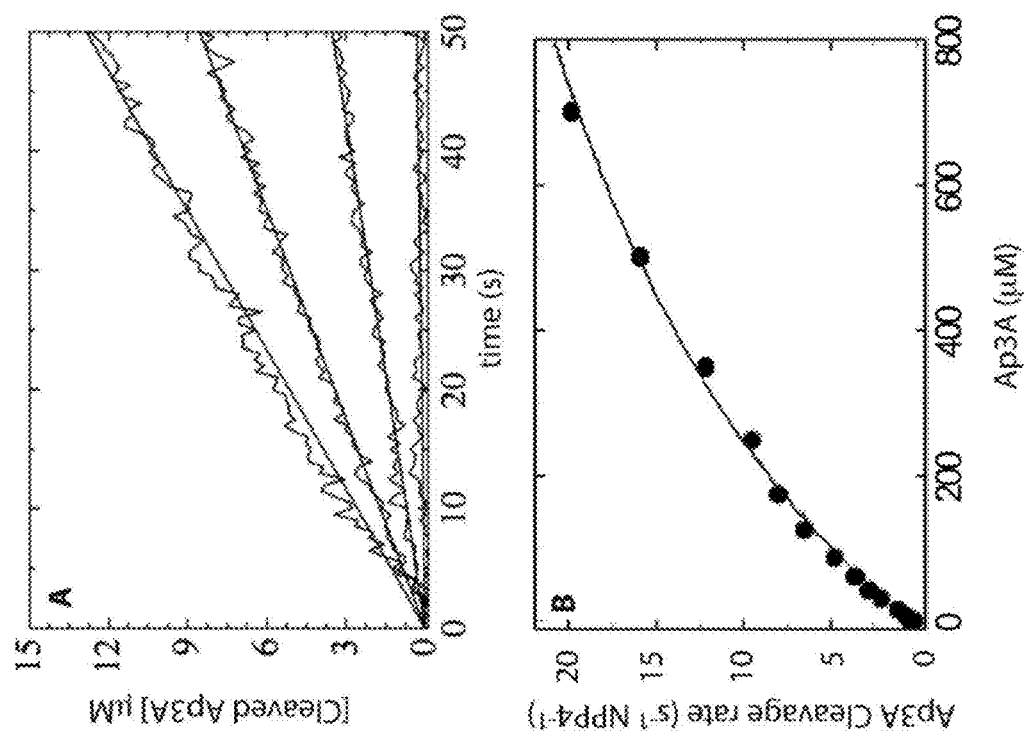
FIG. 3, comprising

To quantitate the steady-state kinetic parameters of NPP4, we measured time courses of Ap3A and Ap4A cleavage using two detection methods. The first is a chromatographic separation by HPLC over a C18 resin (FIG. 2). The second is a spectrophotometric assay (Lobaton et al., 1975, Biochem Biophys Res Commun 1975; 67(1): 279-86) in which Ap3A hydrolysis is quantitated from changes in absorbance at 259 nm (FIG. 3). Analysis of the reaction components at various time points by HPLC reveals a single cleavage site with both substrates, such that hydrolysis products are AMP and ADP with Ap3A substrate, and AMP and ATP with Ap4A substrate (FIG. 2), consistent with a proposed mechanism of NPP cleavage based on alkaline phosphatase homology modeling (Gijsbers et al., 2001, J Biol Chem 276:1361-8). A mutant NPP4 in which the active site threonine, homologous to the catalytic threonine in NPP2, is replaced with alanine (NPP4-T70A) did not cleave diadenosine polyphosphates when assayed by either the linked assay, HPLC, or by absorbance, consistent with threonine 70 acting as the catalytic residue, and with previously published models of NPP catalytic mechanism (Gijsbers et al., 2003, FEBS Lett 538:60-4; Saunders et al., 2011, The Journal of Biological Chemistry 286:30130-41). Time courses of product formation are linear over short time scales and yield substrate Michaelis constant ($K_M$) values of ~800 µM for Ap3A (FIG. 3B) and ~200 µM for Ap4A (Table 1). The maximum catalytic turnover rate ($k_{cat}$) values are ~4 $s^{-1}$ for Ap3A (FIG. 3B) and ~1 $s^{-1}$ for Ap4A (Table 1). Time courses of product formation display deviations from linearity over long time scales due to substrate depletion, and possibly, product inhibition (De La Cruz et al., 2000, Biophys J 79:1524-9).

TABLE 1

Enzyme Kinetics

| | Ap3A Hydrolysis by NPP4 | | Ap4A Hydrolysis by NPP4 | |
|---|---|---|---|---|
| | Value | Std. Error | Value | Std. Error |
| $k_{cat}$ ($s^{-1}$ NPP4$^{-1}$) | 4.2 | ±0.4 | 0.78 | ±0.01 |
| $K_M$ (µM) | 843.1 | ±132 | 209.9 | ±3 |
| $k_{cat}/K_M$ | 5.0 × 10$^3$ | | 3.7 × 10$^3$ | |

Physiologic Role of NPP4 in Platelet Aggregation

Figure 4:
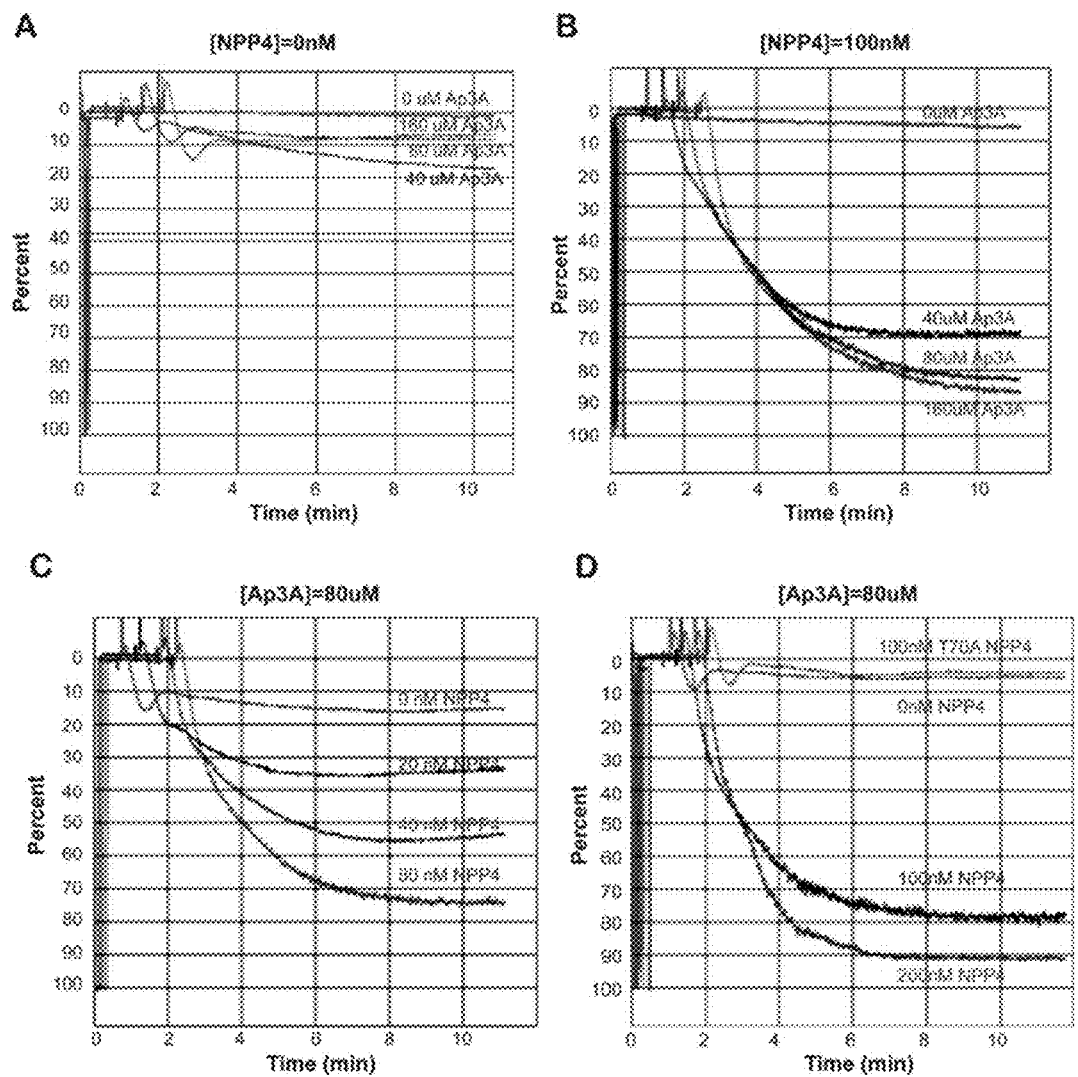
FIG. 4, comprising

To determine the physiologic response of NPP4 catalytic activity, we measured platelet aggregation in PRP by light transmission aggregometry (LTA). Exposure of platelets to exogenous Ap3A alone at concentrations up to 160 µM triggers a primary wave of aggregation without degranulation, followed by rapid disaggregation (FIG. 4A). In the presence of 100 nM of NPP4, Ap3A induces both the primary and secondary waves of aggregation in a concentration-dependent fashion, with 70% maximum aggregation obtained with just 40 µM Ap3A and with greater than 80% maximum aggregation obtained at Ap3A concentrations of 80 µM or higher (FIG. 4B). Platelet aggregation likewise demonstrated a concentration-dependent response to NPP4 at 80 µM Ap3A, with 80% maximum aggregation occurring at 100 nM NPP4 and 90% occurring at 200 nM NPP4 (FIGS.

4C 4D). Importantly, an inactive T70A mutant of NPP4, incapable of Ap3A hydrolysis, shows no effect on platelet aggregation in the presence of 80 µM Ap3A (FIG. 4D), establishing that the aggregatory effects of NPP4 are linked to the catalytic activity of the enzyme. Combined with the concentration-dependent response of Ap3A, these data strongly indicate that the proaggregatory effect of NPP4 is linked to ADP generation via Ap3A hydrolysis.

Figure 5:
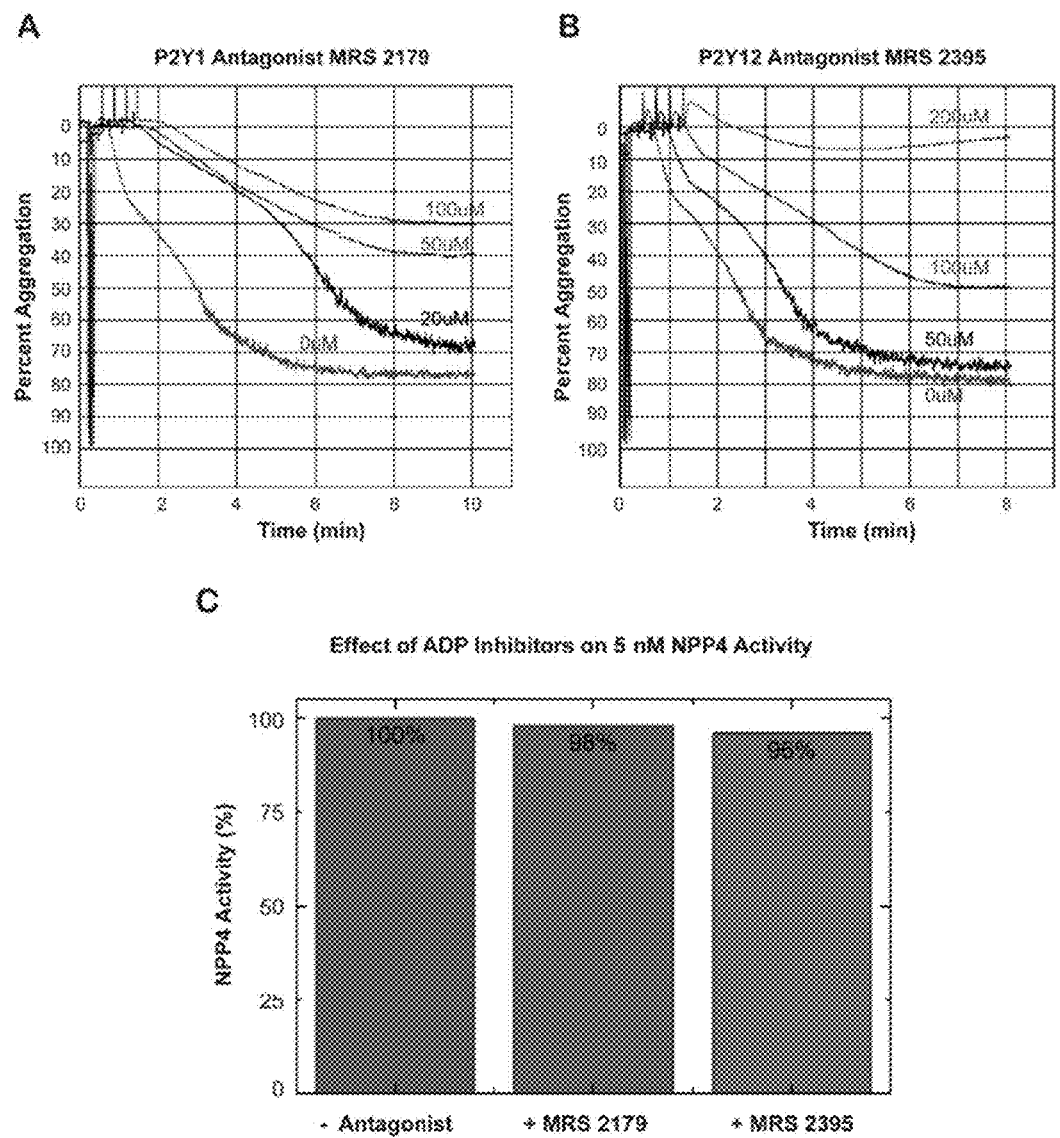
FIG. 5, comprising

To confirm that the observed effect of NPP4 on platelet aggregation was due to generation of ADP by hydrolysis of Ap3A, experiments were conducted in the presence of ADP receptor blockade (FIG. 5). The inclusion of the P2Y1 receptor antagonist, MRS 2179 with 50 nM NPP4 and 80 µM Ap3A showed concentration-dependent inhibition of platelet aggregation with MRS 2179 at concentrations ranging from 0 to 100 µM (FIG. 5A). Similarly, the P2Y12 receptor antagonist, MRS 2395 showed concentration-dependent inhibition of platelet aggregation with complete inhibition occurring at a final concentration of 200 µM (FIG. 5B). Neither ADP receptor antagonist demonstrated any significant inhibition of NPP4-mediated enzymatic activity in the colorimetric hydrolysis assay against the synthetic substrate pNP-TMP at concentrations an order of magnitude greater than those measured in the aggregation experiment (FIG. 5C). Accordingly, the results of these experiments are consistent with the explanation that NPP4 mediates its effect on platelet aggregation via hydrolysis of Ap3A to ADP.

Figure 6:
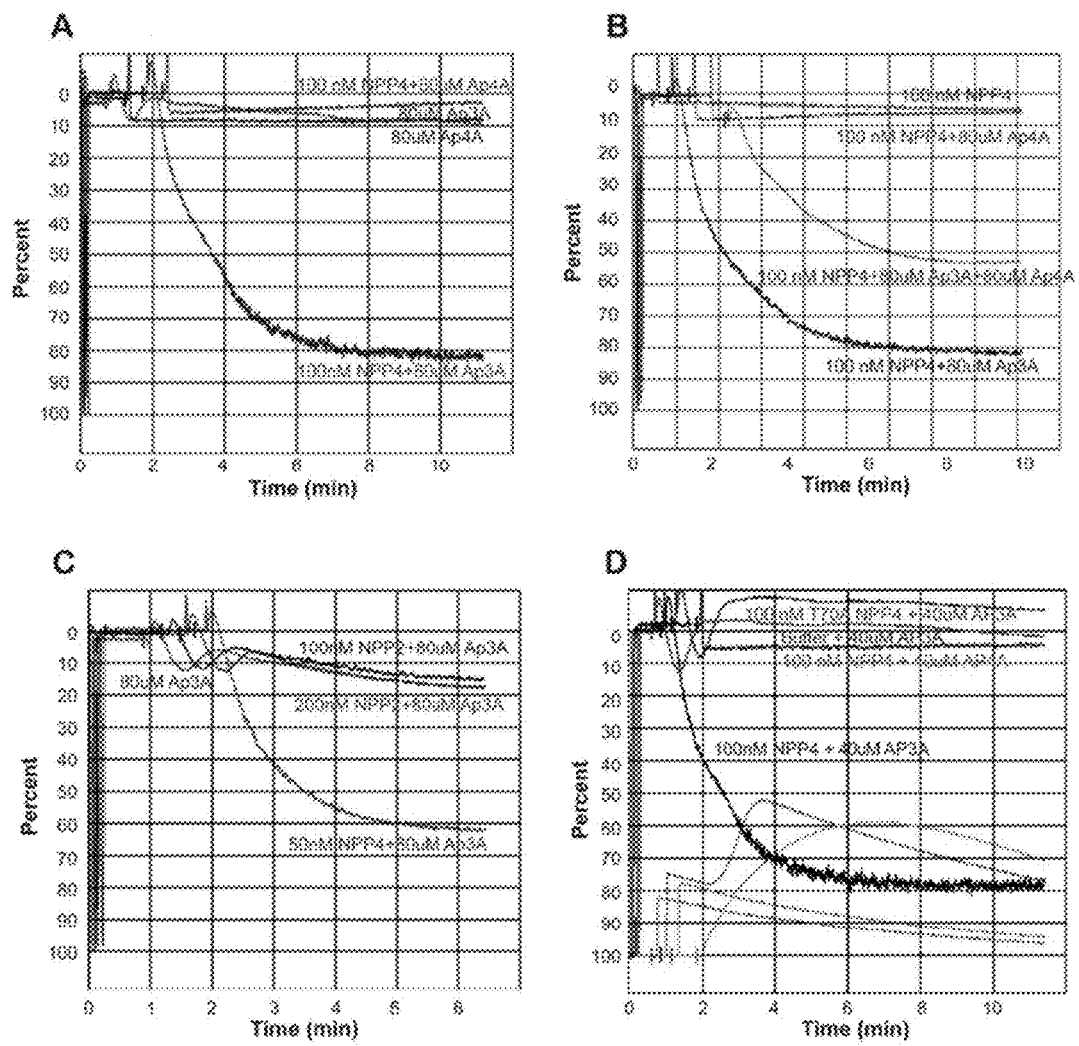
FIG. 6, comprising

To test the effects of Ap4A hydrolysis by NPP4 on platelet aggregation platelet aggregation induced by various concentrations of Ap4A and NPP4 was measured by LTA. Ap4A at 8004, either alone or in the presence of 100 nM NPP4, had no apparent positive effect on aggregation (FIG. 6A) in marked contrast to NPP4 in the presence of 80 µM Ap3A (FIG. 6A). However, Ap4A in the presence of Ap3A blunts the proaggregatory effects of Ap3A and NPP4 on platelet aggregation. As seen in FIG. 6B, platelet aggregation in the presence of 100 nM NPP4 and both 80 µM Ap3A and 80 µM Ap4A (FIG. 6B) is roughly half of the aggregation induced by 100 nM NPP4 and 80 µM Ap3A without Ap4A present (FIG. 6B). These findings are consistent with previous published studies demonstrating that Ap4A inhibits the effects of ADP on platelet aggregation via antagonism of P2Y1 and P2Y12 receptors (Chang et al., 2010, Thromb Res 125:159-65), and further support the idea that NPP4 induces aggregation via the generation of ADP from Ap3A hydrolysis. Additionally, Ap4A competes with Ap3A for the NPP4 active site.

Next, it was confirmed that NPP2, which had no measurable effect on Ap3A hydrolysis in enzymatic studies (data not shown), also had no effect on platelet aggregation. In the presence of 80 µM Ap3A, NPP2 at concentrations up to 200 nM had no measurable effects on platelet aggregation, in marked contrast to NPP4 (FIG. 6C). To directly link the physiologic effects of Ap3A hydrolysis by NPP4 to platelet degranulation, lumi aggregometry was performed to follow platelet aggregation and dense granule release simultaneously with LTA. ATP release and platelet aggregation were simultaneously seen only in samples containing both NPP4 and Ap3A (FIG. 6D), where the sharp sigmoidal increase in luminescence indicates a sudden burst of ATP in the extracellular compartment via platelet degranulation. NPP4 hydrolysis of Ap3A yields AMP and ADP, not ATP. In marked contrast, samples containing NPP4 and Ap4A (FIG. 6D) exhibit no measurable platelet aggregation, and only a gradual parabolic rise of luminescence, indicating that the dense granule contents are not released, and that the observed rise results instead from NPP4 hydrolysis of Ap4A to AMP and ATP. These studies establish that Ap3A hydrolysis by NPP4 induces platelet degranulation and the second wave of platelet activation, resulting in irreversible platelet aggregation characteristic of thrombus formation.

NPP4 Overcomes Platelet Aggregation Deficits Induced by NSAIDs and a Storage Pool Disorder NPP4 rescues platelets exposed to NSAIDs. Platelet-rich plasma was prepared from blood from an individual who had consumed an 800 mg dose of ibuprofen 12 hours prior to collection. Light transmission aggregometry in the presence of 3 µM ADP shows a primary wave of aggregation followed by rapid disaggregation (FIG. 8A). Addition of 20 nM NPP4 results in normalization of ADP-induced aggregation, suggesting that low nanomolar levels of NPP4 are able to generate sufficient ADP from Ap3A to rescue platelets that have been affected by NSAID-induced cyclooxygenase-1 inhibition. The aggregation of platelets unexposed to NSAIDs in the presence of 3 uM ADP is shown to compare the aggregation under identical experimental conditions as in FIG. 8A (FIG. 8B). NPP4 is able to partially overcome a platelet storage pool disorder (FIG. 8C). Platelet rich plasma was prepared from blood of a patient donor with a mild platelet storage pool disorder. This patient has a mild bleeding diathesis attributed to mild platelet dysfunction in which aggregation in response toarachidonic acid is normal but there is no response to epinephrine and shows an attenuated secondary wave of aggregation with subsequent disaggregation in response to ADP. Weak aggregation followed by disaggregation is seen in response to 2.5 µM ADP. The addition of 50 nM NPP4 improves maximum amplitude of aggregation from approximately 40% to approximately 65% with less prominent disaggregation noted over the 10-minute time course of the experiment. These results suggest that in storage pool disorders there are sufficient quantities of Ap3A released to react with low nanomolar levels of NPP4 to trigger a physiologic response.

Example 2: NPP4 is on the Surface of Human Monocytes

Monocytes have an established role in thrombosis and hemostasis. Under conditions of platelet activation, P-selectin is transposed from α-granules onto the platelet outer membrane. Platelet microparticles bud off the platelet membrane containing P-selectin, and these particles, or P-selectin from other sources, recognizes P-selectin glycoprotein ligand-1 (PSGL-1) expressed on monocytes. The recognition of PSGL-1 by monocytes leads to the expression of circulating tissue factor, an important pro-thrombotic enzyme that stimulates the intrinsic coagulation cascade. To determine if monocytes may express NPP4 on their surfaces, flow cytometry was performed on human bone marrow samples, and gated on the monocyte specific marker CD14 and NPP4. As seen in FIG. 9, over 70% of CD14+ cells also show strong expression of NPP4. In contrast, only 3% of CD33+ granulocytes express NPP4 (data not shown), indicating NPP4 protein expression appears specific to monocytic cells. The identification of NPP4 on hematopoietic cells having an established role in hemostasis further supports a physiologic role of NPP4 in coagulation.

The disclosures of each and every patent, patent application, and publication cited herein are hereby incorporated herein by reference in their entirety. While the invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method of treating hemophilia in a human subject in need thereof, the method comprising administering to the subject a therapeutically effective amount of an isolated soluble NPP4 polypeptide comprising amino acid residues 1-407 of SEQ ID NO:1.

2. The method of claim 1, wherein the NPP4 polypeptide is a soluble recombinant NPP4 polypeptide.

3. The method of claim 1, wherein said NPP4 polypeptide lacks the NPP4 transmembrane domain.

4. The method of claim 1, wherein the NPP4 polypeptide consists of amino acid residues 1-407 of SEQ ID NO:1.

5. The method of claim 1, wherein the NPP4 polypeptide is administered in combination with at least one other agent useful in treating bleeding.

6. The method of claim 1, wherein the NPP4 polypeptide is administered acutely or chronically.

7. The method of claim 1, wherein the NPP4 polypeptide is administered locally, regionally or systemically.

* * * * *

SEQUENCE LISTING

<160> NUMBER OF SEQ ID NOS: 2

<210> SEQ ID NO 1
<211> LENGTH: 453
<212> TYPE: PRT
<213> ORGANISM: Homo sapiens

<400> SEQUENCE: 1

```
Met Lys Leu Leu Val Ile Leu Leu Phe Ser Gly Leu Ile Thr Gly Phe
1               5                   10                  15

Arg Ser Asp Ser Ser Ser Leu Pro Pro Lys Leu Leu Leu Val Ser
            20                  25                  30

Phe Asp Gly Phe Arg Ala Asp Tyr Leu Lys Asn Tyr Glu Phe Pro His
            35                  40                  45

Leu Gln Asn Phe Ile Lys Glu Gly Val Leu Val Glu His Val Lys Asn
        50                  55                  60

Val Phe Ile Thr Lys Thr Phe Pro Asn His Tyr Ser Val Thr Gly
65                  70                  75                  80

Leu Tyr Glu Glu Ser His Gly Ile Val Ala Asn Ser Met Tyr Asp Ala
                85                  90                  95

Val Thr Lys Lys His Phe Ser Asp Ser Asn Asp Lys Asp Pro Phe Trp
            100                 105                 110

Trp Asn Glu Ala Val Pro Ile Trp Val Thr Asn Gln Leu Gln Glu Asn
        115                 120                 125

Arg Ser Ser Ala Ala Ala Met Trp Pro Gly Thr Asp Val Pro Ile His
    130                 135                 140

Asp Thr Ile Ser Ser Tyr Phe Met Asn Tyr Asn Ser Ser Val Ser Phe
145                 150                 155                 160

Glu Glu Arg Leu Asn Asn Ile Thr Met Trp Leu Asn Ser Asn Pro
                165                 170                 175

Pro Val Thr Phe Ala Thr Leu Tyr Trp Glu Glu Pro Asp Ala Ser Gly
            180                 185                 190

His Lys Tyr Gly Pro Glu Asp Lys Glu Asn Met Ser Arg Val Leu Lys
        195                 200                 205

Lys Ile Asp Asp Leu Ile Gly Asp Leu Val Gln Arg Leu Lys Met Leu
    210                 215                 220

Gly Leu Trp Glu Asn Leu Asn Val Ile Ile Thr Ser Asp His Gly Met
225                 230                 235                 240

Thr Gln Cys Ser Gln Asp Arg Leu Ile Asn Leu Asp Ser Cys Ile Asp
                245                 250                 255

His Ser Tyr Tyr Thr Leu Ile Asp Leu Ser Pro Val Ala Ala Ile Leu
            260                 265                 270

Pro Lys Ile Asn Arg Thr Glu Val Tyr Asn Lys Leu Lys Asn Cys Ser
        275                 280                 285

Pro His Met Asn Val Tyr Leu Lys Glu Asp Ile Pro Asn Arg Phe Tyr
    290                 295                 300

Tyr Gln His Asn Asp Arg Ile Gln Pro Ile Ile Leu Val Ala Asp Glu
305                 310                 315                 320

Gly Trp Thr Ile Val Leu Asn Glu Ser Ser Gln Lys Leu Gly Asp His
                325                 330                 335

Gly Tyr Asp Asn Ser Leu Pro Ser Met His Pro Phe Leu Ala Ala His
            340                 345                 350

Gly Pro Ala Phe His Lys Gly Tyr Lys His Ser Thr Ile Asn Ile Val
        355                 360                 365
```

```
Asp Ile Tyr Pro Met Met Cys His Ile Leu Gly Leu Lys Pro His Pro
    370                 375                 380

Asn Asn Gly Thr Phe Gly His Thr Lys Cys Leu Leu Val Asp Gln Trp
385                 390                 395                 400

Cys Ile Asn Leu Pro Glu Ala Ile Ala Ile Val Ile Gly Ser Leu Leu
                405                 410                 415

Val Leu Thr Met Leu Thr Cys Leu Ile Ile Ile Met Gln Asn Arg Leu
            420                 425                 430

Ser Val Pro Arg Pro Phe Ser Arg Leu Gln Leu Gln Glu Asp Asp Asp
        435                 440                 445

Asp Pro Leu Ile Gly
    450

<210> SEQ ID NO 2
<211> LENGTH: 863
<212> TYPE: PRT
<213> ORGANISM: Homo sapiens

<400> SEQUENCE: 2

Met Ala Arg Arg Ser Ser Phe Gln Ser Cys Gln Ile Ile Ser Leu Phe
1               5                   10                  15

Thr Phe Ala Val Gly Val Asn Ile Cys Leu Gly Phe Thr Ala His Arg
            20                  25                  30

Ile Lys Arg Ala Glu Gly Trp Glu Glu Gly Pro Pro Thr Val Leu Ser
        35                  40                  45

Asp Ser Pro Trp Thr Asn Ile Ser Gly Ser Cys Lys Gly Arg Cys Phe
    50                  55                  60

Glu Leu Gln Glu Ala Gly Pro Pro Asp Cys Arg Cys Asp Asn Leu Cys
65                  70                  75                  80

Lys Ser Tyr Thr Ser Cys Cys His Asp Phe Asp Glu Leu Cys Leu Lys
                85                  90                  95

Thr Ala Arg Gly Trp Glu Cys Thr Lys Asp Arg Cys Gly Glu Val Arg
            100                 105                 110

Asn Glu Glu Asn Ala Cys His Cys Ser Glu Asp Cys Leu Ala Arg Gly
        115                 120                 125

Asp Cys Cys Thr Asn Tyr Gln Val Val Cys Lys Gly Glu Ser His Trp
    130                 135                 140

Val Asp Asp Asp Cys Glu Glu Ile Lys Ala Ala Glu Cys Pro Ala Gly
145                 150                 155                 160

Phe Val Arg Pro Pro Leu Ile Ile Phe Ser Val Asp Gly Phe Arg Ala
                165                 170                 175

Ser Tyr Met Lys Lys Gly Ser Lys Val Met Pro Asn Ile Glu Lys Leu
            180                 185                 190

Arg Ser Cys Gly Thr His Ser Pro Tyr Met Arg Pro Val Tyr Pro Thr
        195                 200                 205

Lys Thr Phe Pro Asn Leu Tyr Thr Leu Ala Thr Gly Leu Tyr Pro Glu
    210                 215                 220

Ser His Gly Ile Val Gly Asn Ser Met Tyr Asp Pro Val Phe Asp Ala
225                 230                 235                 240

Thr Phe His Leu Arg Gly Arg Glu Lys Phe Asn His Arg Trp Trp Gly
                245                 250                 255

Gly Gln Pro Leu Trp Ile Thr Ala Thr Lys Gln Gly Val Lys Ala Gly
            260                 265                 270

Thr Phe Phe Trp Ser Val Val Ile Pro His Glu Arg Arg Ile Leu Thr
        275                 280                 285
```

```
Ile Leu Gln Trp Leu Thr Leu Pro Asp His Glu Arg Pro Ser Val Tyr
    290                 295                 300

Ala Phe Tyr Ser Glu Gln Pro Asp Phe Ser Gly His Lys Tyr Gly Pro
305                 310                 315                 320

Phe Gly Pro Glu Met Thr Asn Pro Leu Arg Glu Ile Asp Lys Ile Val
                    325                 330                 335

Gly Gln Leu Met Asp Gly Leu Lys Gln Leu Lys Leu His Arg Cys Val
                340                 345                 350

Asn Val Ile Phe Val Gly Asp His Gly Met Glu Asp Val Thr Cys Asp
            355                 360                 365

Arg Thr Glu Phe Leu Ser Asn Tyr Leu Thr Asn Val Asp Ile Thr
370                 375                 380

Leu Val Pro Gly Thr Leu Gly Arg Ile Arg Ser Lys Phe Ser Asn Asn
385                 390                 395                 400

Ala Lys Tyr Asp Pro Lys Ala Ile Ile Ala Asn Leu Thr Cys Lys Lys
                405                 410                 415

Pro Asp Gln His Phe Lys Pro Tyr Leu Lys Gln His Leu Pro Lys Arg
                420                 425                 430

Leu His Tyr Ala Asn Asn Arg Ile Glu Asp Ile His Leu Leu Val
    435                 440                 445

Glu Arg Arg Trp His Val Ala Arg Lys Pro Leu Asp Val Tyr Lys Lys
450                 455                 460

Pro Ser Gly Lys Cys Phe Phe Gln Gly Asp His Gly Phe Asp Asn Lys
465                 470                 475                 480

Val Asn Ser Met Gln Thr Val Phe Val Gly Tyr Gly Pro Thr Phe Lys
                485                 490                 495

Tyr Lys Thr Lys Val Pro Pro Phe Glu Asn Ile Glu Leu Tyr Asn Val
                500                 505                 510

Met Cys Asp Leu Leu Gly Leu Lys Pro Ala Pro Asn Asn Gly Thr His
            515                 520                 525

Gly Ser Leu Asn His Leu Leu Arg Thr Asn Thr Phe Arg Pro Thr Met
530                 535                 540

Pro Glu Glu Val Thr Arg Pro Asn Tyr Pro Gly Ile Met Tyr Leu Gln
545                 550                 555                 560

Ser Asp Phe Asp Leu Gly Cys Thr Cys Asp Asp Lys Val Glu Pro Lys
                565                 570                 575

Asn Lys Leu Asp Glu Leu Asn Lys Arg Leu His Thr Lys Gly Ser Thr
                580                 585                 590

Glu Glu Arg His Leu Leu Tyr Gly Arg Pro Ala Val Leu Tyr Arg Thr
            595                 600                 605

Arg Tyr Asp Ile Leu Tyr His Thr Asp Phe Glu Ser Gly Tyr Ser Glu
610                 615                 620

Ile Phe Leu Met Pro Leu Trp Thr Ser Tyr Thr Val Ser Lys Gln Ala
625                 630                 635                 640

Glu Val Ser Ser Val Pro Asp His Leu Thr Ser Cys Val Arg Pro Asp
                645                 650                 655

Val Arg Val Ser Pro Ser Phe Ser Gln Asn Cys Leu Ala Tyr Lys Asn
                660                 665                 670

Asp Lys Gln Met Ser Tyr Gly Phe Leu Phe Pro Pro Tyr Leu Ser Ser
                675                 680                 685

Ser Pro Glu Ala Lys Tyr Asp Ala Phe Leu Val Thr Asn Met Val Pro
    690                 695                 700
```

```
Met Tyr Pro Ala Phe Lys Arg Val Trp Asn Tyr Phe Gln Arg Val Leu
705                 710                 715                 720

Val Lys Lys Tyr Ala Ser Glu Arg Asn Gly Val Asn Val Ile Ser Gly
            725                 730                 735

Pro Ile Phe Asp Tyr Asp Tyr Asp Gly Leu His Asp Thr Glu Asp Lys
            740                 745                 750

Ile Lys Gln Tyr Val Glu Gly Ser Ser Ile Pro Val Pro Thr His Tyr
        755                 760                 765

Tyr Ser Ile Ile Thr Ser Cys Leu Asp Phe Thr Gln Pro Ala Asp Lys
    770                 775                 780

Cys Asp Gly Pro Leu Ser Val Ser Ser Phe Ile Leu Pro His Arg Pro
785                 790                 795                 800

Asp Asn Glu Glu Ser Cys Asn Ser Ser Glu Asp Glu Ser Lys Trp Val
            805                 810                 815

Glu Glu Leu Met Lys Met His Thr Ala Arg Val Arg Asp Ile Glu His
            820                 825                 830

Leu Thr Ser Leu Asp Phe Phe Arg Lys Thr Ser Arg Ser Tyr Pro Glu
        835                 840                 845

Ile Leu Thr Leu Lys Thr Tyr Leu His Thr Tyr Glu Ser Glu Ile
        850                 855                 860
```